(12) United States Patent
McCormick

(10) Patent No.: US 12,204,491 B2
(45) Date of Patent: *Jan. 21, 2025

(54) DATA ARCHIVAL SYSTEM AND METHOD

(71) Applicant: Cigna Intellectual Property, Inc., Wilmington, DE (US)

(72) Inventor: Jeffrey R. McCormick, Cheshire, CT (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,246

(22) Filed: Oct. 9, 2023

(65) Prior Publication Data

US 2024/0037065 A1 Feb. 1, 2024

Related U.S. Application Data

(63) Continuation of application No. 17/540,502, filed on Dec. 2, 2021, now Pat. No. 11,789,898, which is a continuation of application No. 16/730,535, filed on Dec. 30, 2019, now Pat. No. 11,200,196, which is a continuation-in-part of application No. 16/156,590, filed on Oct. 10, 2018, now abandoned.

(51) Int. Cl.
*G06F 16/11* (2019.01)
*G06F 11/34* (2006.01)
*G06F 16/16* (2019.01)

(52) U.S. Cl.
CPC ........ *G06F 16/113* (2019.01); *G06F 11/3476* (2013.01); *G06F 16/162* (2019.01)

(58) Field of Classification Search
None
See application file for complete search history.

(56) References Cited

U.S. PATENT DOCUMENTS

| | | | |
|---|---|---|---|
| 6,539,402 B1 * | 3/2003 | Sorenson | ............ G06F 11/1471 |
| 7,529,784 B2 | 5/2009 | Kavuri | |
| 8,255,395 B2 | 8/2012 | Park | |
| 8,745,010 B2 | 6/2014 | Chan | |
| 9,043,576 B2 | 5/2015 | St Laurent | |
| 9,697,080 B2 | 7/2017 | Franklin | |
| 9,940,329 B2 | 4/2018 | Schnase | |
| 10,089,179 B2 | 10/2018 | Franklin | |

(Continued)

OTHER PUBLICATIONS

Loomis, Timothy P. "Audit History and Time-Slice Archiving in an Object DBMS for Laboratory Databases." Hewlett Packard Journal 48 (1997): 80-80. (Year: 1997).*

(Continued)

*Primary Examiner* — Uyen T Le
(74) *Attorney, Agent, or Firm* — Miller Johnson

(57) ABSTRACT

An apparatus may be configured to determine an industry object model for a data set of an enterprise; and generate an archive package for an archive time point by generating a set of global objects such that each global object of the set of global objects is represented in the data set and for a respective data source of the set of data sources, generating a set of data source objects based on the industry object model, associating the set of data source objects with the set of global objects, and storing, in the archive package, the set of data source objects and the associated global objects for the respective data source.

18 Claims, 15 Drawing Sheets

(56) References Cited

U.S. PATENT DOCUMENTS

| | | |
|---|---|---|
| 10,158,894 B2 | 12/2018 | Nair |
| 10,306,308 B2 | 5/2019 | Nair |
| 10,467,070 B2 | 11/2019 | Iqbal |
| 2003/0167273 A1 | 9/2003 | Alexander |
| 2004/0177319 A1 | 9/2004 | Horn |
| 2006/0010195 A1 | 1/2006 | Mamou |
| 2006/0069717 A1 | 3/2006 | Mamou |
| 2008/0016026 A1 | 1/2008 | Farber |
| 2008/0109448 A1* | 5/2008 | Aboel-Nil ............ G06Q 10/107 |
| 2010/0250633 A1 | 9/2010 | Hannuksela |
| 2011/0137869 A1 | 6/2011 | Coldicott |
| 2011/0238935 A1 | 9/2011 | Meehan |
| 2012/0197631 A1 | 8/2012 | Ramani |
| 2012/0246126 A1* | 9/2012 | Rodriguez ............. G06F 16/21 707/694 |
| 2015/0012498 A1 | 1/2015 | Oberoi |
| 2015/0254256 A1 | 9/2015 | St Laurent |
| 2015/0339370 A1* | 11/2015 | Onusko ................ G06F 16/284 707/722 |
| 2016/0092535 A1 | 3/2016 | Kuchibhotla |
| 2016/0140131 A1 | 5/2016 | Chen |
| 2016/0335331 A1 | 11/2016 | Schnase |
| 2017/0004152 A1 | 1/2017 | Kommisetty |
| 2017/0116556 A1 | 4/2017 | Brower, Jr. |
| 2017/0168920 A1 | 6/2017 | Werth |
| 2018/0039640 A1 | 2/2018 | St Laurent |
| 2018/0246944 A1 | 8/2018 | Yelisetti |
| 2018/0276232 A1* | 9/2018 | Dhanasekaran ........ G06F 16/25 |
| 2019/0370136 A1 | 12/2019 | Smeaton |
| 2019/0391957 A1 | 12/2019 | Ye |
| 2020/0311270 A1 | 10/2020 | Gryaznov |
| 2022/0229821 A1 | 7/2022 | Greenshpan |

OTHER PUBLICATIONS

Czejdo, Bogdan, et al. ",,Data Warehouses with Dynamically Changing Schemas and Data Sources". Proceedings of the 3rd International Economic Congress, Opportunieties of Change, Sopot, Poland. 2003. 10 pages (Year: 2003).

Fischer, et al., "Information Management Along the Lifecycle of Data and Application Systems: Challenges and Solution Approaches." ICIQ. 2009, 11 pages (Year: 2009).

* cited by examiner

| Column Name | Description |
|---|---|
| Archive Package ID | 3498573496 : Unique identifier that represents a collection of archived business objects |
| Archive ID | 1283446534839399034 : Unique identifier that represents a business object within the Archive System |
| BO Class | Claim : Maintains the name of the Business Object Class |
| Data Classification ID | Restricted : Business data sensitivity indicator(tag) |
| Archive Date | 2019-03-15T16:37:22Z : Date when the Business Data was created for archive |
| Retention Policy | Claim : Policy assigned to the business object |
| System Id | 18364 : System source Identifier |
| Checksum | 23893470489538580 : Checksum value of the business data (payload) to ensure immutability |
| Business Data | Source System Business Data ... |

700 — Archive Metadata fields are the same for all Source Systems

702 — Archive Business Data attributes may be different for each Source System

FIG. 8

DATA ARCHIVAL SYSTEM AND METHOD

CROSS-REFERENCE TO RELATED APPLICATIONS

This application is a continuation of U.S. application Ser. No. 17/540,502 filed Dec. 2, 2021 (now U.S. Pat. No. 11,789,898), which is a continuation of U.S. application Ser. No. 16/730,535 filed Dec. 30, 2019 (now U.S. Pat. No. 11,200,196), which is a continuation-in-part of U.S. application Ser. No. 16/156,590 filed Oct. 10, 2018. The entire disclosures of these applications are incorporated by reference.

FIELD

The disclosure relates to electronic long-term data archival.

BRIEF DESCRIPTION OF THE DRAWINGS

FIG. 8 is an illustration of another example data object in accordance with some example embodiments.

DETAILED DESCRIPTION

A. Introduction

Figure 1:
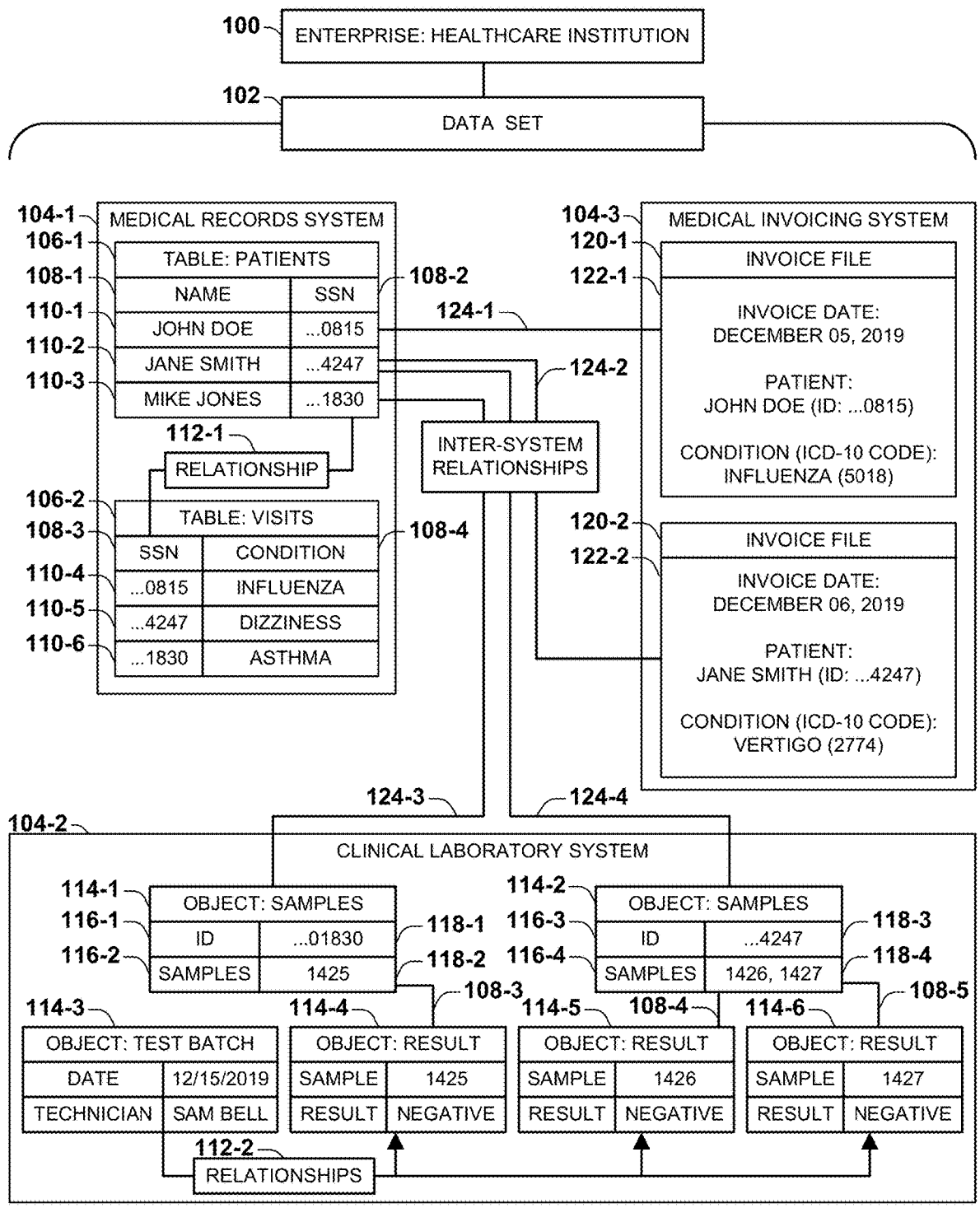
FIG. 1 is an illustration of an example system set for an enterprise.

Within the field of computing, many scenarios involve a data set that is distributed over a set of systems, such as file systems, databases, object graphs, and the like. Each system may include one or more servers, such as file servers, webservers, database servers, etc., where each server stores a portion of the data set in volatile and/or nonvolatile memory. Each server may organize the portion of the data, for example, according to the uses of the data by the server and the processes applied thereto. For example, a relational database server may be configured to store a portion of the data set as a set of tables, each table including a number of attributes (such as columns) and a set of records (such as rows), each record having a value for each attribute. An object server may store the portion of the data set as an object graph, each object including a set of member fields (such as values) and a set of member functions that may be invoked to access or manipulate the set of member fields. A file server may store the portion of the data set as a hierarchically organized set of files, each file including some metadata (such as a filename, dates of creation and modification, and a version history) and binary contents of the file (such as text, images, computer-executable instructions, and the like).

Additionally, an enterprise-level data set or the entire set of academic data of a university, may be provided by a set of services. As a first example, a hospital may provide an organization of services such as medical records, diagnostic laboratory tests, staffing, and insurance and medical invoicing. As a second example, a university may provide an organization of services such as a registrar, student accounts, human resources, and research administration. Each service of the enterprise may organize its data in a manner that is suitable for its role and functionality of the service. For example, in a healthcare institution, some information about an individual may be stored partly in a set of medical records, organized by the services provided and annotations of healthcare providers; partly in a set of laboratory tests, organized according to the tests performed and determined results; partly in staffing records, organized according to the healthcare providers assigned to the individual and the duties performed; and partly in insurance invoicing, organized according to the invoices submitted for insurance reimbursement and the responses of the insurance companies as to coverage.

In such scenarios, respective pairs of systems may be interrelated in an ad-hoc manner, for instance, using different types of identifiers for the identification of matching records. For instance, different systems of a healthcare institution may variously track information about an individual based on the individual's social security number (SSN), an identifier assigned to the individual by the individual's insurance provider, and/or an identifier generated for the user by the healthcare institution.

Additionally, different systems of a healthcare institution may store data about an individual that is overlapping, redundant, synchronized and/or divergent, and/or reflective of different semantics based on the different systems. For example, an individual's healthcare condition may be described in a first way within a clinical laboratory database (such as based on a scientific taxonomy of health conditions), in a second way within staffing records (such as based on a type of care required for the individual), and in a third way within medical invoicing records (such as based on a healthcare reimbursement coding system).

FIG. 1 is an illustration of an example data set 102 for an enterprise 100 such as a healthcare institution.

As shown in FIG. 1, the data set 102 for the enterprise 100 may be distributed over a plurality of systems 104, including a medical records system 104-1, a clinical laboratory system 104-2, and a medical invoicing system 104-3. Each of the systems 104 may store data according to the functionality of the system 104.

As further shown in FIG. 1, the medical records system 104-1 may store its portion of the data set of the enterprise 100 as a relational database including a set of tables 106 that represent different aspects of the stored medical records, such as a "Patients" table 106-1 representing patients and a "Visits" table 106-2 representing patient visits to a healthcare provider. Each table 106 may store a set of attributes 108 and a set of records 110 having a value for each of the attributes 108. For example, the "Patients" table 106-1 includes a "Name" attribute 108-1 and an "SSN" attribute 108-2 for the social security number of an individual, and a first record 110-1 may store a value of "John Doe" for the "Name" attribute 108-1 and a value ending in "0815" for the "SSN" attribute 108-2. The records of the tables 106 may include intra-system relationships 112, such as foreign-key relationships by which corresponding values in corresponding attributes 108 of two records 106 in the same table 106 or different tables 106 may denote a data relationship.

As further shown in FIG. 1, the clinical laboratory system 104-2 may store its portion of the data set of the enterprise 100 as a directed object graph, in which different objects 114 may include a set of key/value pairs, where the keys 116 are the names of the member fields of the objects 114 and the values 118 are the values of the member fields of the objects 114. For example, a first object 114-1 may represent a set of samples submitted by individuals, and may include an "ID" key 116-1 with the social security number of an individual that corresponds to the "SSN" attribute 108-2 of the "Patients" table 106-1 and a "Samples" key 116-2 storing a set of numeric identifiers of samples submitted by the individual for testing. The object set may also include a "Test Batch" object 114-3 representing a batch of samples that were evaluated (e.g., on a certain date and by a certain technician) and that includes relationships 108-2 with a set of other objects 114-4, 114-5, 114-6 indicating the result of each tested sample.

As further shown in FIG. 1, the medical invoicing system 104-3 may store its portion of the data set of the enterprise 100 as a set of invoice files 120, each representing an invoice that has been generated for the services provided to an individual. Each invoice may be represented as an invoice file 120 (e.g., as a document including file contents 122 in a format such as the Portable Document Format (PDF), Hypertext Markup Language (HTML), or Extensible Markup Language (XML)).

As further shown in FIG. 1, the records 110 of the medical records system 104-1, the objects 114 of the clinical laboratory system 104-2, and the invoice files 120 of the medical invoicing system 104-3 may have inter-system relationships 124-2 based on corresponding content. As an example, some objects 114 of the clinical laboratory system 104 may include keys 116 with values 118 that correspond to values of the "SSN" attribute 108-2 of the "Patients" table 106-1. As another example, the invoice files 120 of the medical invoicing system 104-3 may include file contents 122 that correspond to, annotate, document, and/or supplement the visits by the individuals to healthcare providers (such as represented in the "Visits" table 106-2) and/or the tests performed by the clinical laboratory (and the results represented in the clinical laboratory system 104-2). In this manner, the respective data stored by the systems 104 of the enterprise 100 may together comprise the data set 102 of the enterprise 100.

In scenarios such as shown in FIG. 1, a task may arise that is to be applied over the entire data set of the enterprise 100 relating to a certain subset of data. For example, a healthcare institution may endeavor to identify all of the data pertaining to the healthcare services provided to a particular individual, or all of the data relating to a pharmaceutical that may have been administered to a patient population to treat different healthcare conditions. Furthermore, the task may involve capturing a snapshot of the selected data across the entire institution at a particular point in time. For example, an audit of the records of the healthcare institution on a particular date may be requested as part of a legal inquiry.

However, such tasks may be difficult due to the diversity of systems that store the data set. For example, the data of a healthcare institution that pertains to an individual may be stored across a set of tables in databases of a clinical laboratory service; in some objects of an object graph managed by a staffing service; and in a set of flat-structured files stored by an invoice processing service. A task of identifying and capturing a complete data set about the individual may therefore involve the effort of subject-matter experts for each system, each of whom may be able to determine the data pertaining to the individual that is stored by one particular system. Moreover, the identification of the complete data set involving the individual may involve analyzing the interrelationships between such systems (e.g., identifying each invoice in the invoice processing service that involves a laboratory test provided by the clinical laboratory service), and understanding the ad-hoc interrelationships between the systems may involve a subject-matter expert who has a detailed understanding of two or more such interrelated systems.

In the example shown in FIG. 1, a task may involve a request to hold a set of records pertaining to the individual "Jane Smith," identifiable by a social security number ending in 4247. In order to fulfill the task, a first analysis may be conducted of the content of the medical records system 104-1 to determine which tables 106 include records 110 with information about Jane Smith, and to preserve the identified records 110. Additionally, a second analysis may be conducted of the content of the clinical laboratory system 104-2 to identify objects 114 that include data pertaining to "Jane Smith," which may in turn depend upon an understanding both intra-system relationship 112 (such as the relationships of the tables 106 of a relational database) and the inter-system relationship 124-3 between the medical records system 104-1 and the clinical laboratory system 104-2 (such as relating the objects 114 of the clinical laboratory system 104-2 to the "Patients" table 106-1 of the medical records system 104-1 to determine which objects have an "ID" field that corresponds to the "SSN" attribute 108-2 of the "Patients" table 106-1). Additionally, a third analysis may be performed to determine which invoice files 120 of the medical invoicing system 104-3 contain information about invoiced services involving "Jane Doe," such as by examining the file contents 122 of each of the invoice files 120. Such analyses may depend upon a detailed understanding of a subject-matter expert regarding the schema of the relational database, the directed object graph of the clinical laboratory system 104-2, and the invoice files 120 of the medical invoicing system 104-3, each of which may be extensive and complex in an enterprise 100 such as a healthcare institution.

Due to such complexities, the task of identifying and capturing all of the data that pertains to the individual may consume a substantial amount of resources, including the effort and attention of subject-matter experts for each system of the enterprise. The substantial effort involved, particularly for subject-matter experts who may be concurrently handling other tasks, may result in a substantial delay in the completion of the task. In some cases, subject-matter experts may not be available or adequately informed to perform the analyses, and some portions of the requested data may be missed and therefore not included in the results of the task.

B. Archive Packages

Figure 2:
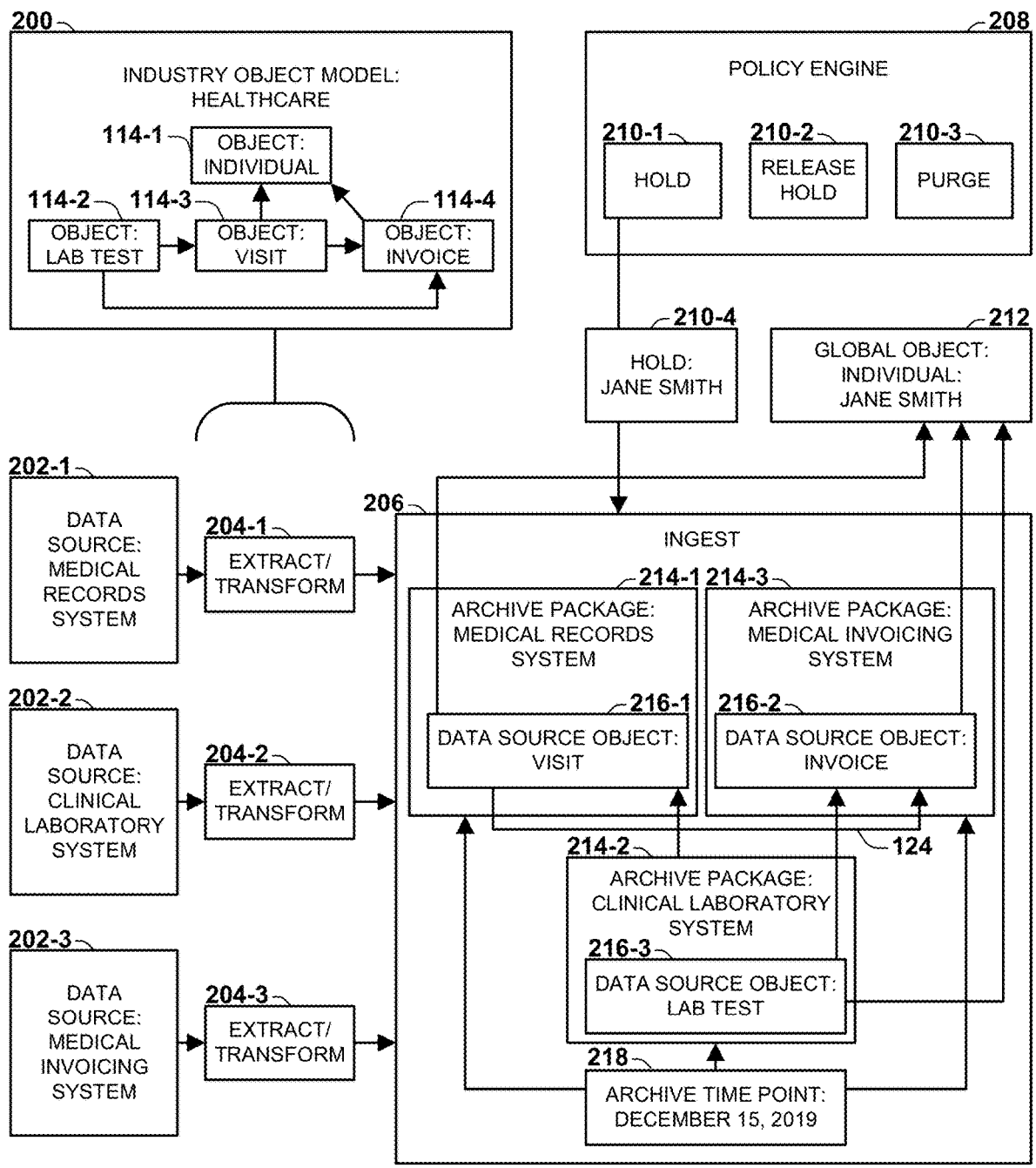
FIG. 2 is an illustration of an example archive package processed over a system set for an enterprise on behalf of a policy engine in accordance with some example embodiments.

FIG. 2 is an illustration of an example archive package processed over a system set for an enterprise on behalf of a policy engine in accordance with some example embodiments.

As shown in FIG. 2, a set of systems 104 that respectively represent data sources 202 may together store a data set 102 of an enterprise 100. The data sources 202 may include a first data source 202-1 for a medical records system, a second data source 202-2 for a clinical laboratory system, and a third data source 202-3 for a medical invoicing system, which may correspond to the respective systems shown in FIG. 1. For the data set of the enterprise 100, an industry object model 200 may be determined based on the industry of the data set (for example, an industry of the enterprise 100), where the industry object model 200 may include a set of objects 114 representing commonplace, familiar, and/or typical entities or units of data within the industry. For example, for the healthcare industry, the industry object model 200 may include an "Individual" object 114-1 representing an individual who is treated by the healthcare system; a "Lab Test" object 114-2 representing a diagnostic clinical test performed by a laboratory for an individual; a "Visit" object 114-3 representing a visit by a healthcare professional; and an "Invoice" object 114-4 representing an invoice submitted for self-pay and/or insurance reimbursement for one or more office visits and/or one or more lab tests for an individual. The industry object model 200 of the industry therefore models, in a familiar and/or holistic manner, all of the entities and/or units of data to which the data of any healthcare institution may pertain.

As further shown in FIG. 2, a policy engine 208 may be provided that stores a set of rules 210 by which various aspects of a policy of the enterprise 100 may be applied to the data set 102 stored by the data sources 202. For example, the rules of the policy engine 208 may include a hold rule 210-1 indicating that certain portions of data are to be held; a hold release rule 210-2 indicating that a hold that was previously applied to certain portions of data is to be released; and a purge rule 210-3 indicating that certain data of the data set 102 of the enterprise 100 (and not subject to a hold rule 210-1) is to be purged from the data set 102.

As further shown in FIG. 2, an instance of a hold rule 210-1 may be initiated by the policy engine 202, such as a request to hold data pertaining to the individual "Jane Smith." Each data source 202 may be subjected to a set of processes to capture an archive package 214 for the data source 202, at an archive time point 218, that represents an archival portion of the data set 102 of the enterprise 100 as a set of data source objects 216 based on each system serving as a data source of the data set 102, and wherein the data source objects 216 are structured according to the industry object model 200. For example, each data source 202 may be subjected to an extract and transform process 204 to transform the data stored by the system into one or more data source objects 216 according to the objects 114 of the industry object model 200. The extracted data source objects 216 may be processed by a system-level ingest process 206 that stores the data source objects 216 in the archive packages 214.

As further shown in FIG. 2, one or more objects may be created as global objects 212, such as an "Individual" global object 212 that may interconnect the data source objects 216 of different data sources 202. The resulting archive package 214 may therefore capture the data requested by the instance 210 of the hold rule 210-1 at the archive time point 218, and according to an industry object model 200 that may be familiar to practitioners in the industry, in accordance with some example embodiments.

C. Technical Effects of Some Example Embodiments

The generation of an archive package 214 as disclosed herein may permit or facilitate some technical effects in some example embodiments.

As a first such example, in some example embodiments, the archive package 214 may enable a representation of a portion of the data set 102 of an enterprise 100 based on an industry object model 200 of objects 114 that may be commonplace, typical, and/or familiar to professionals in the industry, particularly as compared with a physical layout of the corresponding data among the systems 104 of the enterprise 100. For example, healthcare professionals may not readily understand the components and operation of the systems 104 in the example system 104 of FIG. 1, such as the distribution of the clinical laboratory data over a set of objects 114 or the distribution of patient data over a set of relational tables 106. In some cases, the portion of the data set 102 that involves a recognizable topic, such as an individual, may appear to be "shredded" into the physical layout of the data over the myriad of systems 104 of the enterprise 100. Reassembly of a portion of the data to collect information about a topic of interest, such as an individual, may entail a substantial reconstructive process performed by a host of subject-matter experts in each of the systems 104. By contrast, the archive packages 214 discussed herein is based on an industry object model 200, and may encapsulate the data about a topic of interest into a set of data source objects 216 that are familiar to individuals in the industry, such as a first data source object 216-1 representing a patient visit, a second data source object 216-2 representing a clinical laboratory test together with its result, and a third data source object 216-3 representing an invoice, as well as a global object 212 representing an individual to whom all of the data source objects 216 of the archive package 214 relate. The archive package 214 may therefore be accessible and cognizable by users who may not be subject-matter experts in the respective systems 104 over which the data set 102 of the enterprise 100 is physically distributed.

As a second such example, in some example embodiments, the archive package 214 may promote a representation of the data set 102 of an enterprise 100 that may enable both intra-system relationships 112 and inter-system relationships 124, that is, interconnections among portions of the data set 102 stored both within each system 104 and among systems 104. Rather than basing such interconnections on ad-hoc aspects, such as interrelating an attribute 108 of a relational table 106 (such as the "SSN" attribute 108-2) and values 118 of member fields of objects 114, the archive package 214 may instead model both intra-system relationships 112 and inter-system relationships 124 as an object graph among similarly structure data source objects 216. Alternatively or additionally, the data source objects 216 of an archive package 214 may model such intra-system relationships 112 and inter-system relationships 124 as relationships to a global object 212, such that all data source objects 216 of an archive package 214 relating to a topic (as represented by a global object 212) may be identified as the data source objects 216 associated therewith. In some example embodiments, these relationships may be further informed by versioning of the global objects 212 and/or by considering the subset of the collection of data source objects 216 in respective archive packages 214 (each representing a different archive time point) that are associated with a particular global object 212.

As a third such example, in some example embodiments, the archive package 214 may enable a policy engine 208 to apply sets of rules 210 and tasks based thereupon to various portions of the data set 102 of an enterprise 100. In some scenarios, such as the example scenario of FIG. 1, such tasks may be difficult to perform due to the complexities of the physical layout of the data set 102 in the individual systems 104 of the enterprise 100. For example, the policy engine 208 may specify a "Hold" rule 210 indicating that data involving a particular topic, such as an individual patient, is to be preserved for legal inquiry. However, applying the "Hold" rule 210 to each such system 104 may involve the effort of a subject-matter expert in each system 104 who understands the layout of the data within the system 104. By contrast, archive packages 214 that are generated such as disclosed herein may transform the data set 102 of the enterprise 100 into a standardized collection of data source objects 216 and global objects 212 over which the rules 210 may be readily applied. These and other technical effects may be achievable in some example embodiments.

D. Some Example Embodiments

Figure 3:
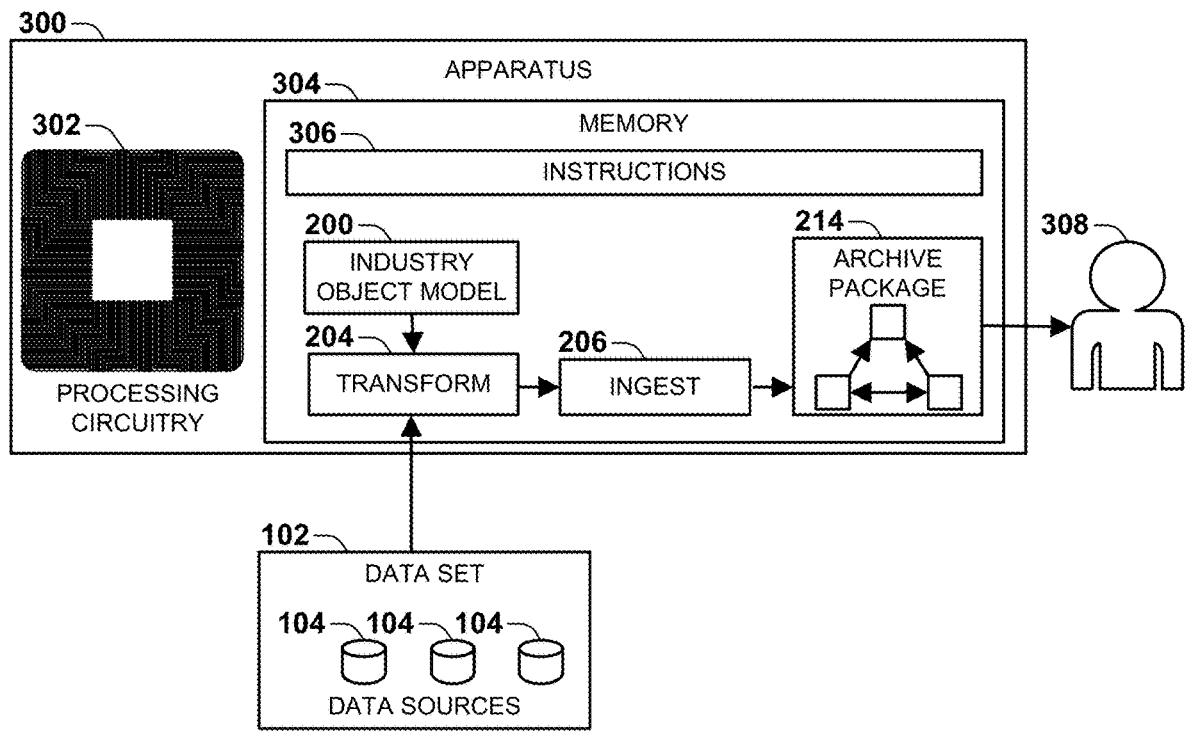
FIG. 3 is a block diagram illustrating an example apparatus in accordance with some example embodiments.

FIG. 3 is a component block diagram of an example apparatus, in accordance with some example embodiments.

As shown in FIG. 3, an example apparatus 300 may include processing circuitry 302 that is capable of executing instructions. The processing circuitry 302 may include, such as hardware including logic circuits; a hardware/software combination, such as a processor executing software; or a combination thereof. For example, a processor may include, but is not limited to, a central processing unit (CPU), a graphics processing unit (GPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

As further shown in FIG. 3, the example apparatus 300 includes a memory 304 storing instructions 306. The memory 304 may include, for example, random-access memory (RAM), read-only memory (ROM), an erasable programmable read-only memory (EPROM), an electrically erasable programmable read-only memory (EEPROM), etc. The memory 304 may be volatile, such as system memory, and/or nonvolatile, such as a hard disk drive, a solid-state storage device, flash memory, or magnetic tape. The instructions 306 stored in the memory 304 may be specified according to a native instruction set architecture of a processor, such as a variant of the IA-32 instruction set architecture or a variant of the ARM instruction set architecture, as assembly and/or machine-language (e.g., binary) instructions; instructions of a high-level imperative and/or declarative language that is compilable and/or interpretable to be executed on a processor; and/or instructions that are compilable and/or interpretable to be executed by a virtual processor of a virtual machine, such as a web browser. A set of non-limiting examples of such high-level languages may include, for example: C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Swift, Eiffel, Smalltalk, Erlang, Ruby, Flash®, Visual Basic®, Lua, MATLAB, SIMULINK, and Python®. Such instructions 306 may also include instructions for a library, resource, platform, application programming interface (API), or the like that is utilized in the generation of an archive package.

The instructions 306 stored in the memory 304, when executed by the processing circuitry 302, cause the apparatus 300 to operate in accordance with some example embodiments.

As a first such example, the instructions 306 may cause the apparatus 300 to archive a data set 102 provided by a set of data sources 202 by determining an industry object model 200 based on an industry of the data set 102 and generating at least one archive package 214 for an archive time point 218 by, for each data source 202, determining archival data of the data source 202 to be archived, transforming 204 the archival data of the data source 202 into a set of data source objects 216 based on the industry object model 202, and storing, in the archive package 214, the set of data source objects 216 for the data source 202; identifying a subset of the data source objects 216 to be purged based on a purge time point 218 and a policy engine 208; and removing the subset of the data source objects 216 from the archive package 214.

As a second such example, the instructions 306 may cause the apparatus 300 to archive a data set 102 provided by a set of data sources 202 by determining an industry object model 200 based on an industry of the data set, and generating at least one archive package for an archive time point by generating a set of global objects that are represented in the data set; for each data source, determining archival data of the data source to be archived, transforming the archival data of the data source into a set of data source objects based on the industry object model, associating the set of data source objects with the set of global objects, and storing the set of global objects and the archive package including the set of data source objects for the data source.

Figure 4A:
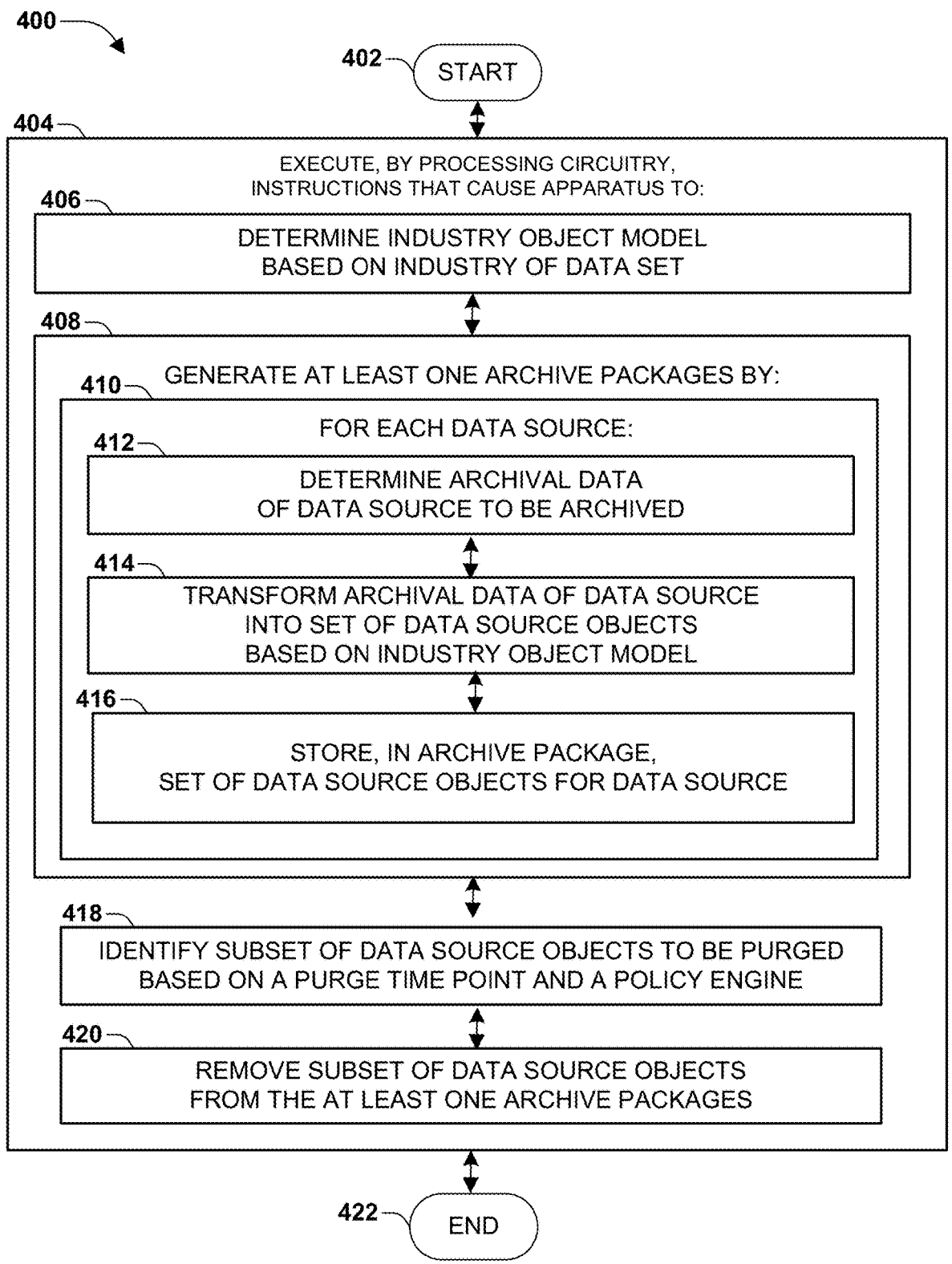
FIG. 4A is a flow diagram illustrating an example method in accordance with some example embodiments.

FIG. 4A is a flow diagram of a first example method 400, in accordance with some example embodiments.

The first example method 400 may be implemented, for example, as a set of instructions 306 that, when executed by processing circuitry 302 of an apparatus 300, cause the apparatus 300 to perform each of the elements of the first example method 400. The first example method 400 begins at 402 and may include executing 404, by processing circuitry 302 of an apparatus 300, instructions 306 that cause the apparatus 300 to perform a set of elements.

For example, the execution of the instructions 306 may cause the apparatus 300 to determine 406 an industry object model based on an industry of the data set.

For example, the execution of the instructions 306 may cause the apparatus 300 to generate 408 at least one archive package 214 for an archive time point 218 by, for each 410 data source, determining 412 archival data of the data source 202 to be archived, transforming 414 the archival data of the data source 202 into a set of data source objects 216 based on the industry object model 200, and storing 416, in the archive package 214, the set of data source objects 216 for the data source 202.

For example, the execution of the instructions 306 may cause the apparatus 300 to identify 418 a subset of the data source objects to be purged based on the purge time point 218 and a policy engine 208, and remove 420 the subset of the data source objects 216 from the at least one archive package 214.

In this manner, the execution of the instructions 306 by the processing circuitry 302 may cause the apparatus 300 to perform the elements of the first example method 400, and so the first example method 400 ends at 422.

Figure 4B:
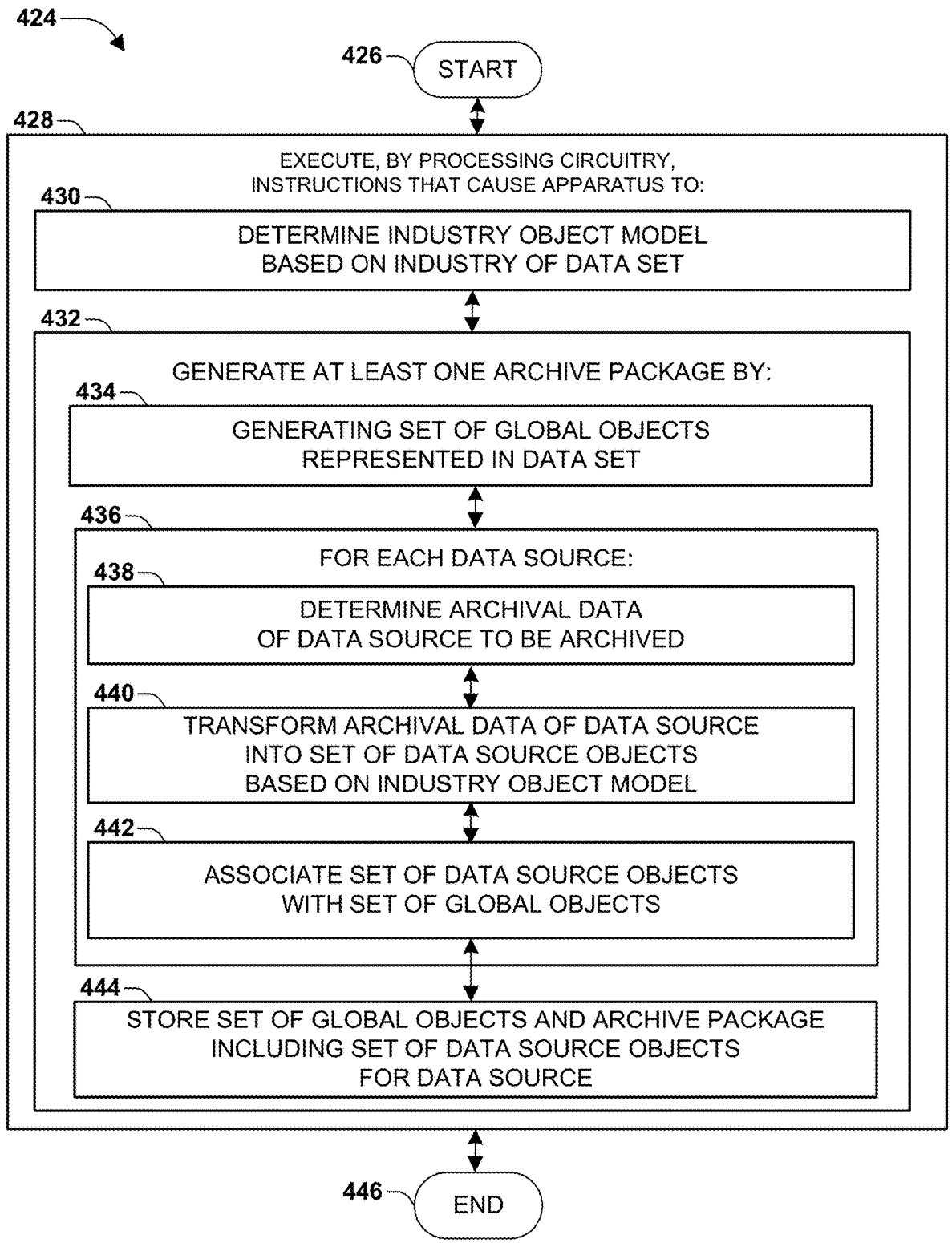
FIG. 4B is a flow diagram illustrating another example method in accordance with some example embodiments.

FIG. 4B is a flow diagram of a second example method 424, in accordance with some example embodiments.

The second example method 424 may be implemented, for example, as a set of instructions 306 that, when executed by processing circuitry 302 of an apparatus 300, cause the apparatus 300 to perform each of the elements of the second example method 418. The second example method 424 begins at 426 and may include executing 428, by processing circuitry 302 of an apparatus 300, instructions 306 that cause the apparatus 300 to perform a set of elements.

For example, the execution of the instructions 306 may cause the apparatus 300 to determine 430 an industry object model 200 based on an industry of the data set 202.

For example, the execution of the instructions 306 may cause the apparatus 300 to generate 432 at least one archive package 214 for an archive time point 218 by generating 434 a set of global objects 212 that are represented in the data set 104; and for each 436 data source, determining 438 archival data of the data source to be archived, transforming 440 the archival data of the data source 202 into a set of data source objects 216 based on the industry object model 200, and associating 442 the set of data source objects 216 with the set of global objects 212; and storing 444 the set of global objects 214 and the at least one archive package 214 including the set of data source objects 216 for each data source 202.

In this manner, the execution of the instructions 306 by the processing circuitry 302 may cause the apparatus 300 to perform the elements of the second example method 424, and so the second example method 424 ends at 446.

Figure 5:
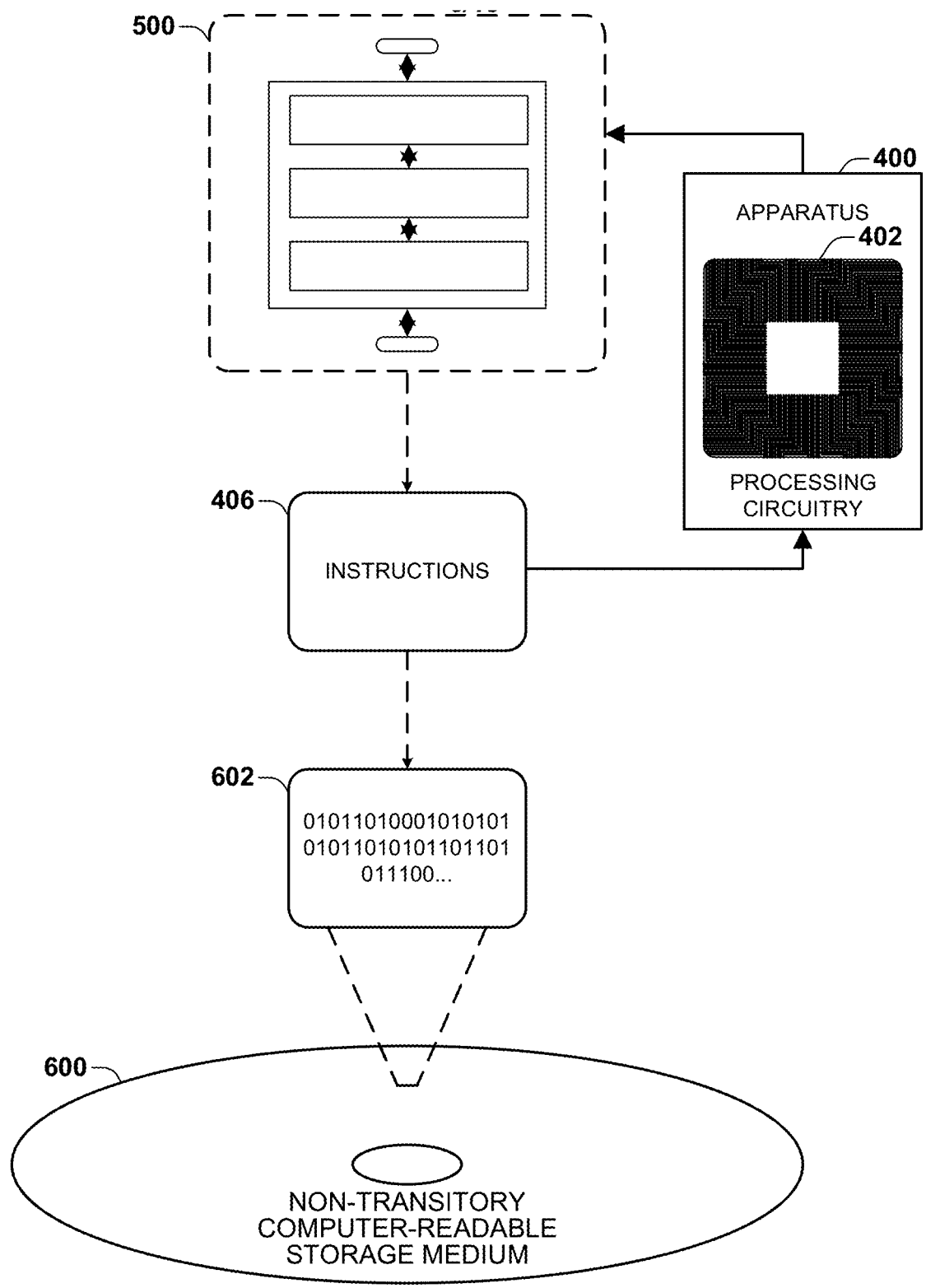
FIG. 5 is an illustration of a non-transitory computer-readable medium in accordance with some example embodiments.

FIG. 5 is an illustration of an example non-transitory computer-readable storage medium 500, in accordance with some example embodiments.

As shown in FIG. 5, the non-transitory computer-readable storage medium 500 may store binary data encoding a set of instructions 506 that, when executed by processing circuitry 502 of an apparatus 500, cause the apparatus 502 to generate an archive package in accordance with some example embodiments. As a first such example, the instructions 504 may encode the elements of the first example method 400 of FIG. 4A. As a first such example, the instructions 504 may encode the elements of the second example method 400 of FIG. 4B. Many such technologies may be utilized in some example embodiments of the present disclosure.

E. Variations

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in some example embodiments (e.g., the example apparatus 300 of FIG. 3, the example method 400 of FIG. 4A, the example method 424 of FIG. 4B, and/or the example non-transitory computer-readable medium 500 of FIG. 5) to confer individual and/or synergistic advantages upon such example embodiments.

E1. Generating Archive Package of Data Source Objects

Some example embodiments may generate the archive package 214 of data source objects 216 in a variety of ways.

In some example embodiments, the industry object model 200 to be used for the data set 102 may be determined in a variety of ways. As a first example, an apparatus 300 may be configured to determine that the systems 104 involved in storing the data set 102 of the enterprise 100 are typically used in a particular industry, such as healthcare institutes, universities, e-commerce businesses, etc., and may choose an industry object model 200 based on the types of systems 104 in use by the enterprise 100. As a second example, an apparatus 300 may be configured to examine the data set 102 to determine the type of industry to which the data set 102 likely applies, such as healthcare records, student records, and online order records, and may choose an industry object model 200 based on the type of data stored by the data set 102. As a third such example, an apparatus 300 may receive a selection by a user 308, from a set of industry object models, 200 of a selected industry object model 200 to be used for a particular data set 102. As used herein, the term "user" includes both individuals and automated processes.

Figure 6:
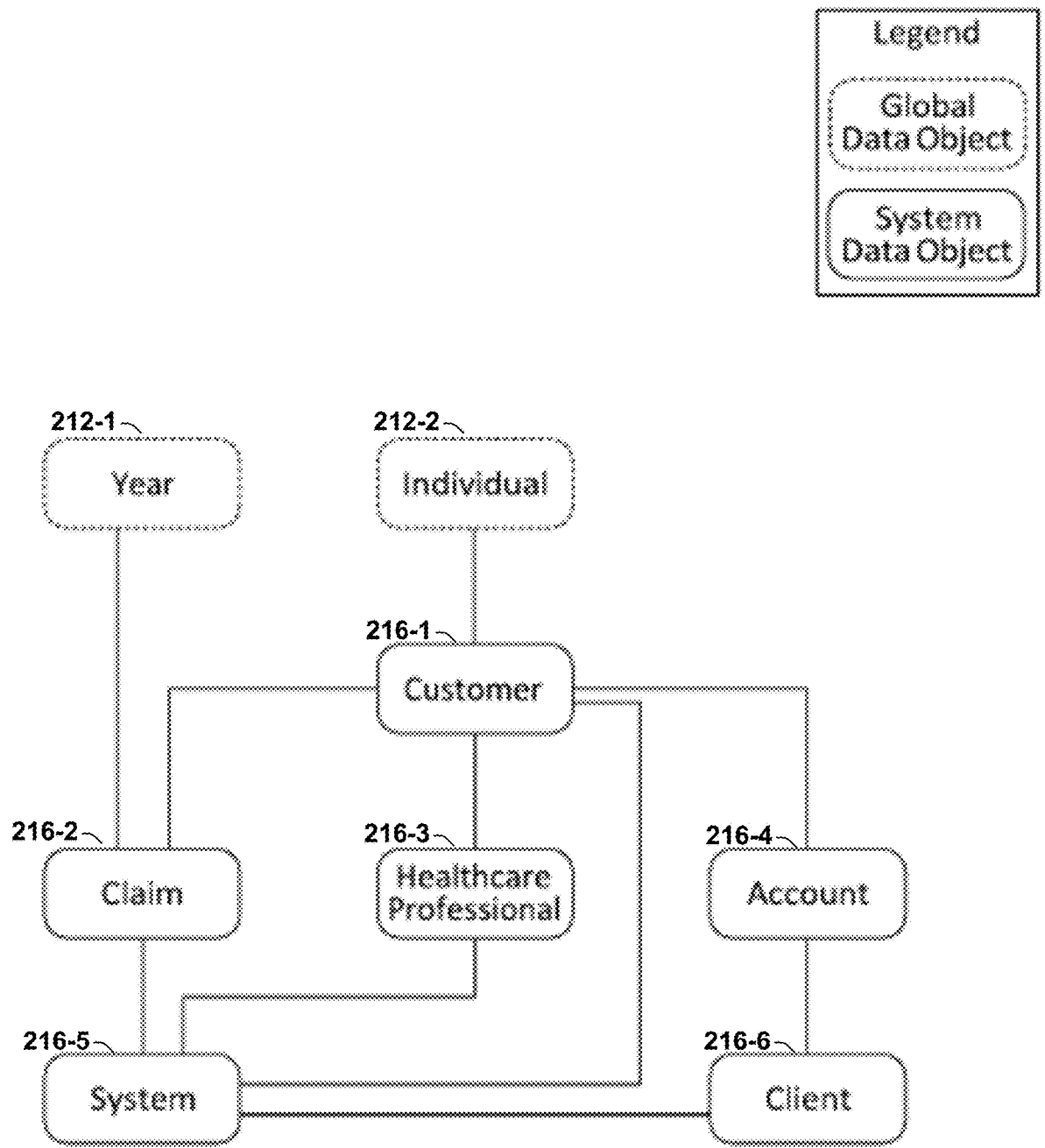
FIG. 6 is an illustration of an example industry object model in accordance with some example embodiments.

FIG. 6 is an illustration of an example industry object model 200 in accordance with some example embodiments.

As shown in FIG. 6, an example industry object model 200 for use with the data set 102 of a healthcare system may include set of data source objects 216 (identified in FIG. 6 as "system data objects") such as a "customer" data source object 216-1, a "healthcare professional" data source object 216-3, and an "account" data source object 216-4. The example industry object model 200 may also include global objects 212 (identified in FIG. 6 as "global data objects") for entities that are likely to pertain to multiple systems 104 in the industry object model 200, such as an "individual" global object 212-2 and a "year" global object 212-1. Intra-system relationships 112 and inter-system relationships 124 may be created between and among the data source objects 216 and global objects 212.

In some example embodiments, an apparatus 300 may be configured to create in the archive package 214, for each data source 202, a system data source object that represents the data source 202, and to associate each data source object 216 that is transformed from the data source 202 with the system data source object 216 for the data source 202. For example, as shown in FIG. 6, a system data source object 216-5 may be created within an archive package 214, and the data source objects 216 generated from a particular system 104 or data source 202 may be associated with the system data source object 216-5.

In some example embodiments, data source objects 216 may be generated from data sources 202 in a variety of ways. For example, an apparatus 300 may receive a transform 204 provided by a system 104 serving as a data source 202, or provided by a user 308. The apparatus 300 may invoke the transform to generate data source objects 216 from the data source 202.

In some example embodiments, an apparatus 300 may be configured to remove, from the data set 104, the data for each entity that is archived in the archive package 214.

Figure 7:
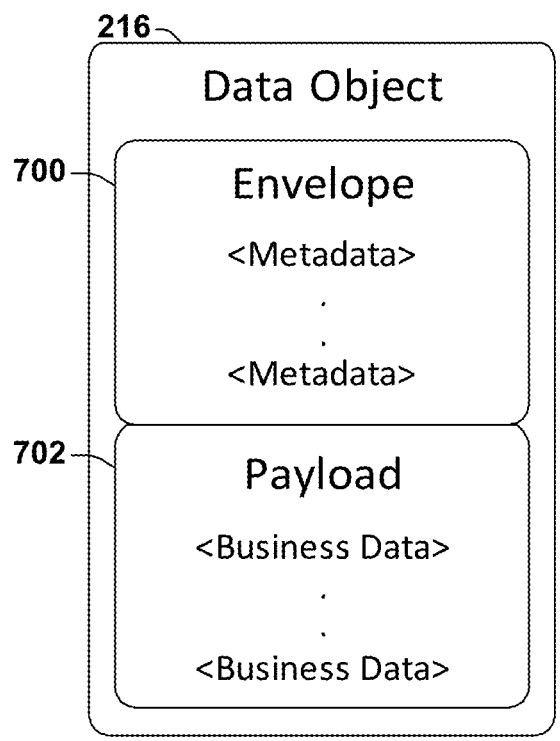
FIG. 7 is an illustration of an example data object in accordance with some example embodiments.

FIG. 7 is an illustration of an example data object in accordance with some example embodiments.

As shown in FIG. 7, a data source object 216 may include an envelope 700 as a record comprising a set of metadata fields (e.g., a set of key/value pairs that define properties that are typical of data source objects 216, such as a universally unique identifier (UUID), a creation date, and a retention policy) and a business data block 702 or payload that stores the data of the data source object 216 as represented by the data source 202. The contents of the business data block 702 may be structured or unstructured data; may include a variety of data types, such as text, images, sounds, videos, documents, numeric or relational tables, and executable code; and may be represented in a variety of data formats, such as JavaScript Object Notation (JSON), Hypertext Markup Language (HTML), Extensible Markup Language (XML), Portable Document Format (PDF), and Open Document Format (ODF).

FIG. 8 is an illustration of another example data object in accordance with some example embodiments.

FIG. 8 provides a more detailed example of a data source object 216, including examples of metadata fields and values that may be included in an envelope 700 and the content of an example business data block 702.

Figure 9:
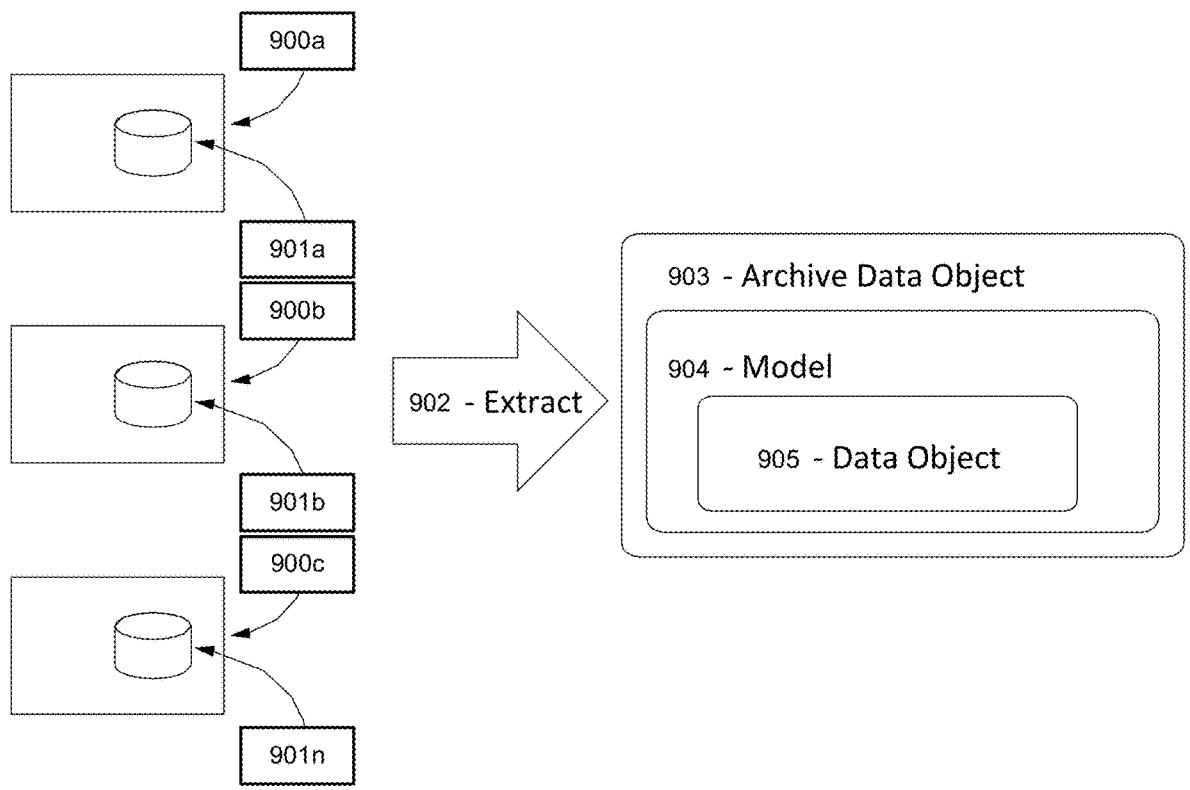
FIG. 9 is an illustration of an example generation of at least one archive package in accordance with some example embodiments.

FIG. 9 is an illustration of an example generation of an archive package in accordance with some example embodiments.

As shown in FIG. 9, an archive package may be generated over a set of data sources 202 in an incremental manner. For example, a set of computer systems 900a, 900b, etc. may store data 901a, 901b, etc. An extraction 902 may be performed over each of the computer systems 900a and a transform 204 may be applied to each system to generate a set of data source objects 216 for an archive package 214 (identified in FIG. 9 as "archive data object" 903) based on the industry object model 200 (identified in FIG. 9 as "model" 904) containing the set of data source objects 216 (identified in FIG. 9 as "data object" 905).

In some example embodiments, the ingesting 206 of data source objects 216 into archive packages 214 may be performed on a per-archive-package basis. In some other example embodiments, the ingesting 206 of data source objects 216 into archive packages 214 may be performed on a holistic basis, that is, as an enterprise-wide ingest process, such as shown in the example scenario of FIG. 2.

In some example embodiments, one archive package 214 may be generated for all data sources 202 at one archive time point 218. In some other example embodiments, each data source 202 may be transformed into an archive package 214. Additionally, the archive time points 218 for the archive packages 214 for each data source 202 may vary; for example, a first data source 202 may periodically archived with a first periodicity (e.g., weekly), and a second data source 202 may be periodically updated with a second periodicity (e.g., monthly), and a third data source 202 may be updated on an ad-hoc basis (e.g., when new instances of purge rules 210 are provided by the policy engine 208).

E2. Global Objects

Some example embodiments may include a set of global objects 212. For example, the global objects 212 specified in an industry object model 200 may represent topics or entities that may be applicable to a substantial number of systems 104, such as individuals in a healthcare system. In some example embodiments, the set of global objects 212 may be generated by identifying an object type to be accessible in the archive package 214 (for example, an individual in a healthcare system) and creating a global object 212 in the set of global objects 212 for each instance of the object type represented in the data set 102 (e.g., each individual who may be a patient in the healthcare system).

In some example embodiments, an apparatus 300 may be configured to create the set of global objects 212 for the data set 102 before associating the set of data source objects 216 of one or more archive packages 214 with the set of global objects 212. Configuring the apparatus 300 to create an entire set of global objects 212 before associating the data source objects 216 with the global objects 212 may ensure that such global objects 212 exist for each such association, and may avoid a scenario, for example, in which a clinical visit record is ingested into the archive package 214 but is unable to be associated with any global object 212 for the individual to whom the clinical visit record applies.

In some example embodiments, an apparatus 300 may be configured to permanently retain the set of global objects 212. That is, even if data source objects 216 related to the topic represented by a particular global object 212 are purged, the apparatus 300 may retain the global object 212 in case future data source objects 216 are later associated with the same topic. For example, an individual may receive care in a healthcare institution at a first date, and a long period of time may pass until a second date at which the individual receives care in the healthcare institution. An apparatus 300 may be configured to retain the global object 212 representing the individual even if the data source objects 216 involving the first visit of the individual are purged due to the lengthy intervening period, such that the individual may be recognized (as per the global object 212 representing the individual) as a previously treated patient while ingesting the data source objects 216 of the second visit.

In some example embodiments, an apparatus 300 may be configured to create a global object 212 for an entity by determining that the set of global objects 212 already includes another global object 212 that corresponds to the entity, and based on the determining, may refrain from creating the global object 212 for the entity in the set of global objects 212. In such manner, the apparatus 300 may de-duplicate the set of global objects 212, for example, by ensuring that duplicate global objects 212 representing the same entity are not created.

In some example embodiments, an apparatus 300 may be configured to generate the set of global objects 212 as a versioned set of global objects, where each entity is represented by at least one global object 212, and each global object 212 includes a version identifier that indicates a version of the entity. For example, different versions of a global object 212 representing an individual may be generated to reflect significant changes to the individual over a time span, such as the individual's name or health status.

In some example embodiments, an apparatus 300 may be configured to generate the versions of a global object 212 by determining, according to a change tracking mechanism of a master data management system, whether an entity that is represented by the global object 212 has changed since the apparatus 300 generated a previous version of the global object 212 of the entity. Based on the determination, the apparatus 300 may create another version of the global object 212 in the set of global objects 212, where the another version of the global object 212 includes a version identifier that follows the version identifier of the previous version of the global object 212.

In some example embodiments, the version identifier of each global object 212 may indicate at least one time point of the entity that is represented by the global object 212. An apparatus 300 may be configured to identify a version of a global object 212 to be associated with each data source object 216 in an archive package 214 based on the archive time point 218 of the archive package 214 and the at least one time point associated with the versions of the global object 212. For example, each version of the global object 212 may include a date range to which each version applies. For data source objects 216 within an archive package 214 that are associated with the global object 212, the applicable version of the global object 212 may be identified based on which version includes a date range that includes the archive time point of the archive package 214.

In some example embodiments, each global object 212 of the set of global objects 212 may be identified by a global object identifier. An apparatus 300 may be configured to associate each data source object 216 with the set of global objects 212 by including the global object identifier of the global object 212 in the data source object 216. For example, a master data management system may include identifiers of individuals in a healthcare system (e.g., based on a social security number, a policy number of an insurance policy that covers each individual, and/or an integer that is arbitrarily assigned by the master data management system), and an apparatus 300 may identify the global object 216 representing each individual based on the identifier assigned to the global object 216 by the master data management system.

E3. Policy Engine and Additional Functionality

Some example embodiments may include a policy engine 208 that is configured to apply a policy to the data set 102. The policy engine 208 may be configured to perform various tasks on the data set 102 to generate, maintain, and/or purge archive packages 214 in accordance with the policy of the enterprise 100, for example, in fulfillment of a legal inquiry.

In some example embodiments, a policy engine 208 may include a set of purge rules 210. For example, the policy engine 208 may define a default purge rule to purge all data source objects 216 that are more than fourteen years old, unless the purge rules 210 indicate that a data source object 216 is to be retained longer and/or purged sooner. An apparatus 300 may be configured to identify a subset of the data source objects 216 for an archive based on the purge rules 210 of the policy engine 208. For example, the apparatus 200 may be configured to evaluate the data source objects to identify the subset of the data source objects 216 to be purged based on a set of purge rules 210 of the policy engine 208, for example, whether data source objects 216 pertaining to a particular individual are to be purged. As an example, the purge rules of the policy engine 208 may include at least one of: a hold rule 210-1 to place a hold on a data source object 216; a hold release rule 210-2 to release a hold on a data source object 216; and a purge rule 210-3 to purge data source objects 216 on which a hold has not been placed.

In some example embodiments, an apparatus 300 may be configured to provide access to archive packages 214 upon request of a user 308. For example, the apparatus 300 may be configured to receive a request to access the archive package 214 based on an access criterion, such as accessing a particular data set object 216 or all data set objects 216 that are associated with a particular global object 212. The apparatus 300 may be configured to provide access to the archive package 214 in response to the request and according to the access criterion.

In some example embodiments, an apparatus 300 may be configured to export an archive package 214, or a portion thereof, upon request of a user 308, and where the request indicates an export format, such as comma-separated values (CSV) or Extensible Markup Language (XML). For example, the apparatus 300 may be configured to export the archive package 214 based on the export format.

In some example embodiments, an apparatus 300 may be configured to store an audit trail of events involving an archive package 214, such as events requested by users 308 and/or performed on an archive package 214 by the apparatus 300. An apparatus 300 may be configured to, responsive to detecting an event involving the archive package 214, log the event in the audit trail. Alternatively or additionally, an apparatus 300 may be configured to receive, from a user 308, a selection of a subset of events to be logged in the audit trail, such as events that involve accessing particular data source objects 216 or global objects 212 and/or particular types of access, such as creating, altering, and/or deleting a data source object 216 or global object 212. The apparatus 300 may be configured to log events that are within the subset of events to be logged in the audit trail, and to refrain from logging events based on determining that such events are not within the subset of events to be logged in the audit trail. Many such forms of policy engines 202 and additional functionality may be included in some example embodiments.

E4. Example Archive Package Systems

Figure 10:
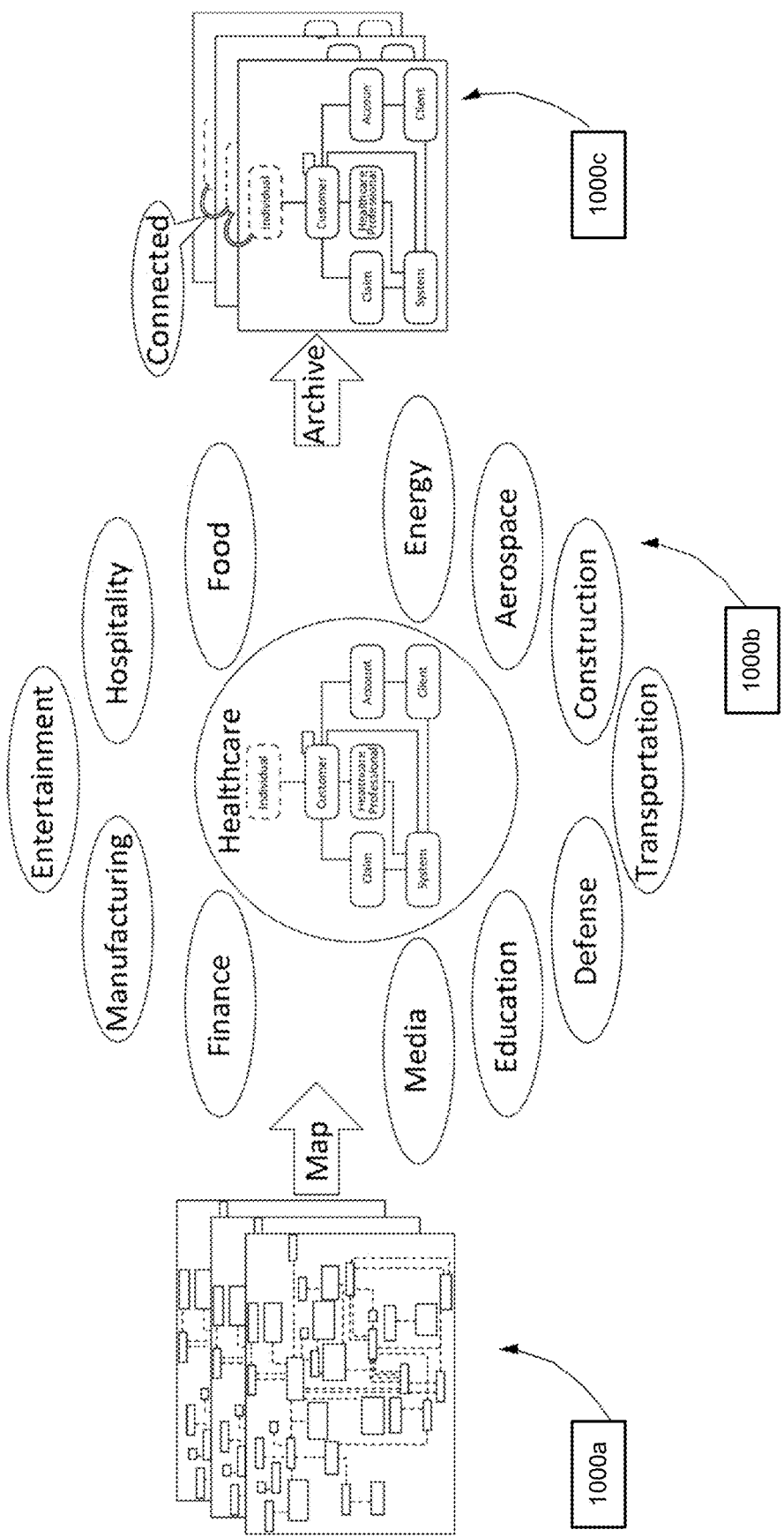
FIG. 10 is an illustration of an example generation of an archive package from a set of systems in accordance with some example embodiments.

FIG. 10 is an illustration of an example generation of an archive package from a set of systems in accordance with some example embodiments.

As shown in FIG. 10, a set of systems 104 (identified in FIG. 10 as "source systems" 1000*a*) comprising an enterprise 1000 may be processed according to an industry object model (identified in FIG. 10 as a "meta model") selected from an industry model object set 1000*b* to generate a set of archive packages (identified in FIG. 10 as an "archive repository").

Figure 11:
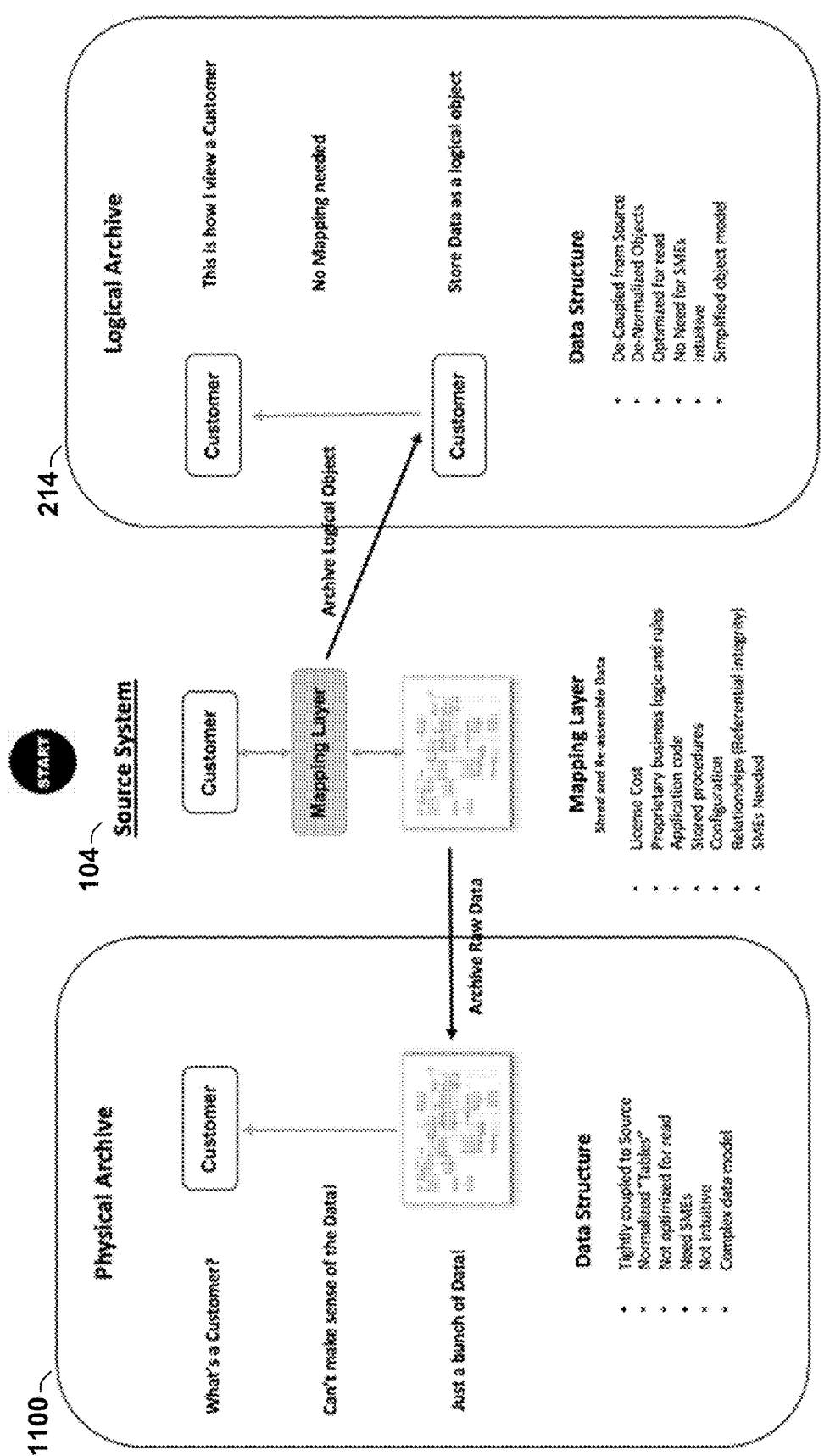
FIG. 11 is an illustration of an example generation of an archive package from a set of systems in accordance with some example embodiments.

FIG. 11 is an illustration of an example generation of an archive package from a set of systems in accordance with some example embodiments.

As shown in FIG. 11, a system 104 (identified in FIG. 11 as a "source system") may store an archive of a set of objects 116, but may do so according to a physical archive 1100 that is organized in accordance with the native layout of the system 104. For example, the physical archive 1100 may be processed through a mapping layer to replicate the relational database structure of a relational database, such as a set of tables 106 and record 110, a directed object graph of objects 116, or a set of files such as invoice files 120. However, a physical archive 1100 that replicates the physical layout of the servers 104 may be difficult to access and/or examine, for example, to apply policies of a policy engine 208, as discussed herein. Instead, the system 104 may be processed as a data source 204 to generate an archive package 214 (identified in FIG. 11 as a "logical archive") as a set of data source objects 216, which may be more readily accessed and/or examined, for instance, by a policy engine 208, as discussed herein.

The example shown in FIG. 11 illustrates some potential technical effects that some example embodiments may achieve in the archive package 214 as compared with the physical archive 1100. As a first such example, the objects in the archive package 214 may resemble the types of entities that exist within the industry object model of the industry of the enterprise 100 and the data set 102 of the enterprise 100, such that a user 308 who is not a subject matter expert in the plurality of system 104 of the enterprise 100 may be familiar with the data source objects 216 and may readily examine and work with the archive packages 214. By contrast, the data in the physical archive 1100 is "shredded" over the captured set of systems 104, and may present difficulty for a user 308 who is not familiar with the systems 104 of the enterprise 100 in examining the contents of the physical archive 1100 and the data contained therein. As a second such example, the data source objects 216 within the archive packages 214 may be easily interrelated as a directed object graph, including through global objects 212, whereas both intra-system relationships 112 and inter-system relationships 124 may be more difficult to capture and understand in a physical archive 1100 of the disparate systems 104 of the enterprise 100. As a third such example, policies such as purge rules 210 may be readily applied to the data source objects 216 contained within the archive packages 214, for example to fulfill tasks such as legal inquiries over the data set 102 of the enterprise 100, whereas applying such policies to the data contained in a physical archive 1100 of the systems 104 of the enterprise 100 may be more difficult to develop and apply in a holistic manner.

Figure 12:
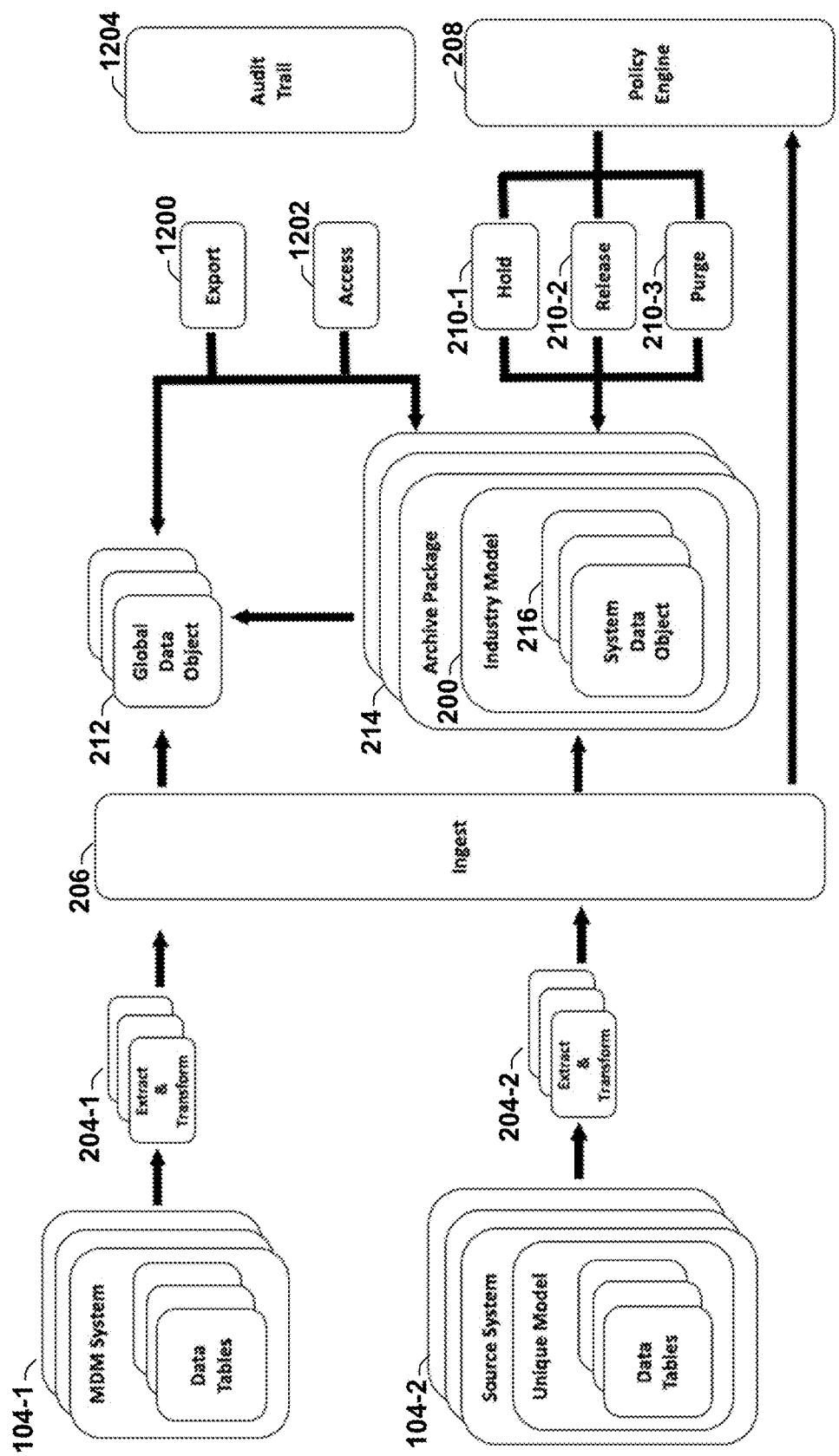
FIG. 12 is an illustration of an example system in accordance with some example embodiments.

FIG. 12 is an illustration of an example system in accordance with some example embodiments.

As shown in FIG. 12, a set of source systems 104-2 may store portions of a data set 102 of an enterprise 100. An apparatus 300 may be configured to process each source system 104 as a data source 202, for example, by applying an extract and transform 204-2 to each data source 202 and ingesting 206 the data source objects 216 into an archive package 214 structured according to an industry object model 200. Additionally, the apparatus 300 may examine a master data management system 104-1 (identified in FIG. 12 as an "MDM system") to determine a set of entities represented therein, and an extract and transform 204-1 may be applied to the master data management system 104-1 to ingest 206 a set of global objects 212 (identified in FIG. 12 as "global data objects"). A policy engine 208 may include a set of purge rules 210, including a hold rule 210-1, a hold release rule 210-2, and a purge rule 210-3, and the apparatus 300 may be configured to apply the purge rules 210 of the policy engine 208 to the archive packages 214. The apparatus 300 may also provide interfaces to export 1200 and access 1202 the archive packages 214, as well as the global objects 212 related to the data source objects 216 within the archive packages 214. The apparatus 300 may also be configured to generate and maintain an audit trail 1204 of the events arising with respect to the archive packages 214.

Figure 13:
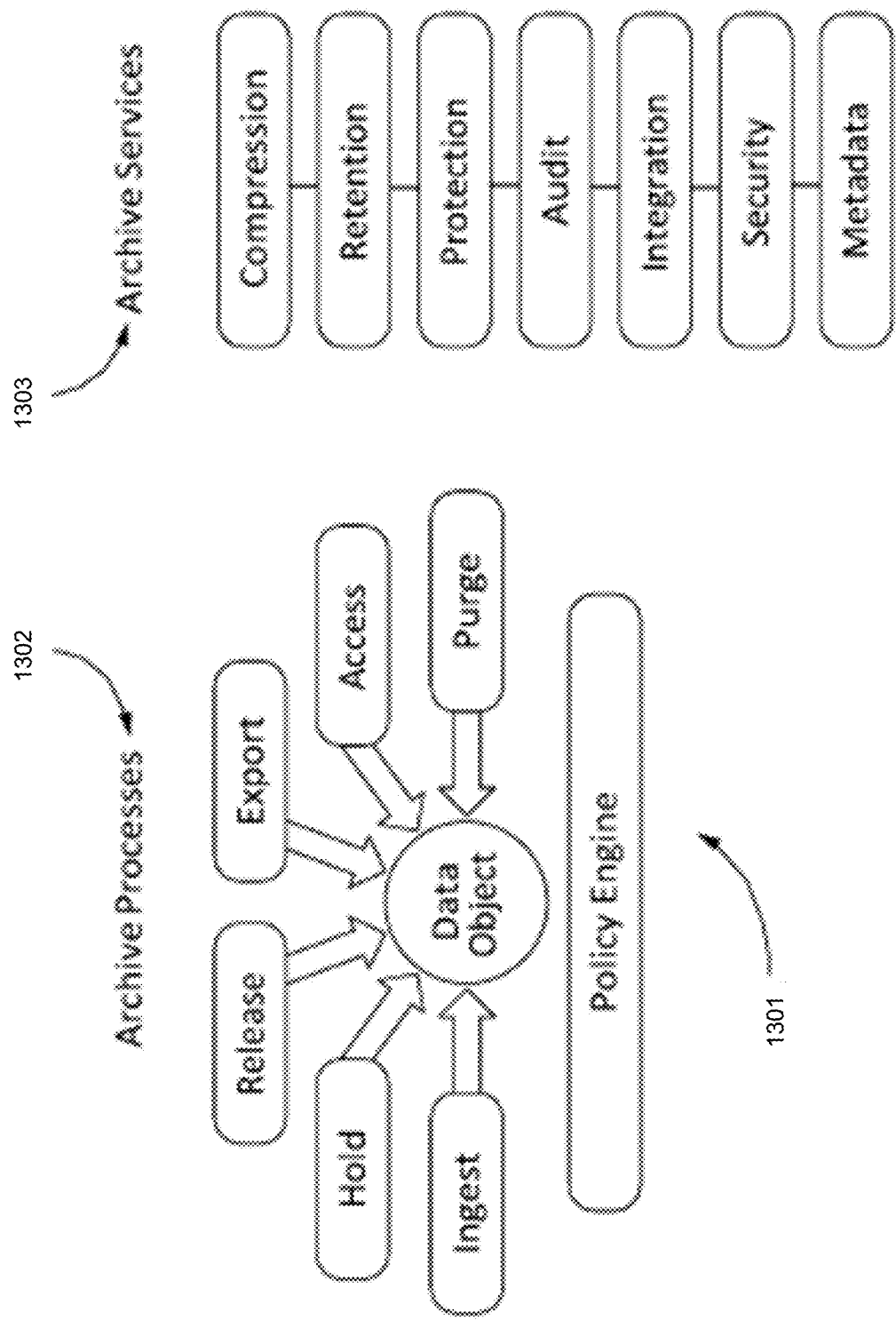
FIG. 13 is an illustration of another example system in accordance with some example embodiments.

FIG. 13 is an illustration of another example system in accordance with some example embodiments.

As shown in FIG. 13, a policy engine 1301 may include a set of archive processes 1302 that may be applied to the data source objects 216 of an archive package 214, as well as a set of archive services 1303, such as compression, retention, protection, auditing, integration with other systems, security, and a maintenance of metadata. These and other types of functionality may be provided in some example embodiments.

F. Example Computing Environment

Figure 14:
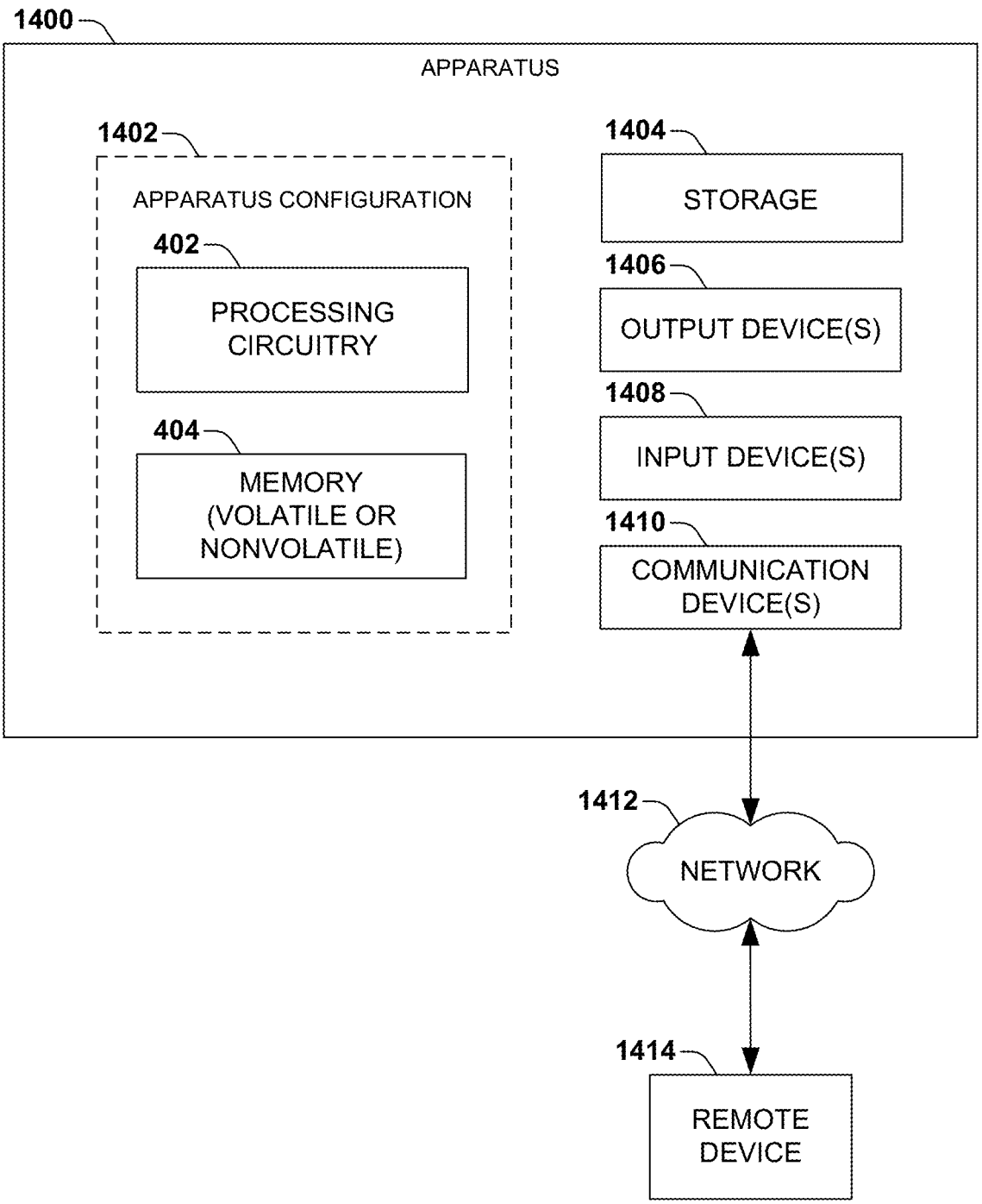
FIG. 14 is an illustration of an example apparatus in which some example embodiments may be implemented.

FIG. 14 is an illustration of an example apparatus in which some example embodiments may be implemented.

FIG. 14 and the following discussion provide a brief, general description of a suitable computing environment to implement embodiments of one or more of the provisions set forth herein. The operating environment of FIG. 14 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 14 illustrates an example of an apparatus configured as, or to include, one or more embodiments, such as the example embodiments provided herein. In one apparatus configuration 1402, the apparatus 1400 may include processing circuitry 402 and memory 404. Depending on the exact configuration and type of computing device, memory 404 may be volatile (such as RAM, for example), nonvolatile (such as ROM, flash memory, etc., for example) or some combination of the two.

In some example embodiments, an apparatus 1400 may include additional features and/or functionality. For example, an apparatus 1400 may also include additional storage (e.g., removable and/or non-removable) including, but not limited to, magnetic storage, optical storage, and the like. Such additional storage is illustrated in FIG. 14 by storage 1404. In some example embodiments, computer-readable instructions to implement one or more embodiments provided herein may be stored in the memory 404 and/or the storage 1404.

In some example embodiments, the storage 1404 may be configured to store other computer readable instructions to implement an operating system, an application program, and the like. Computer-readable instructions may be loaded in memory 404 for execution by processing circuitry 402, for example. Storage may include volatile and nonvolatile, removable and non-removable media implemented in any method or technology for storage of information such as computer readable instructions or other data. Storage may include, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which may be used to store the desired information and which can be accessed by apparatus 1400. Any such computer storage media may be part of apparatus 1400.

In some example embodiments, an apparatus 1400 may include input device(s) 1414 such as keyboard, mouse, pen, voice input device, touch input device, infrared cameras, video input devices, and/or any other input device. Output device(s) 1412 such as one or more displays, speakers, printers, and/or any other output device may also be included in device 1402. Input device(s) 1414 and output device(s) 1412 may be connected to device 1402 via a wired connection, wireless connection, or any combination thereof. In one embodiment, an input device or an output device from another computing device may be used as input device(s) 1414 or output device(s) 1412 for computing device 1402.

In some example embodiments, an apparatus 1400 may be connected by various interconnects, such as a bus. Such interconnects may include a Peripheral Component Interconnect (PCI), such as PCI Express, a Universal Serial Bus (USB), Firewire (IEEE 1394), an optical bus structure, and the like. In another embodiment, components of an apparatus 1400 may be interconnected by a network. For example, memory 404 may be comprised of multiple physical memory units located in different physical locations interconnected by a network.

In some example embodiments, an apparatus 1400 may include one or more communication device(s) 1410 by which the apparatus 1400 may communicate with other devices. Communication device(s) 1410 may include, for example, a modem, a Network Interface Card (NIC), an integrated network interface, a radio frequency transmitter/receiver, an infrared port, a USB connection, or other interfaces for connecting the apparatus 1400 to other computing devices, including remote devices 1414. Communication device(s) 1410 may include a wired connection or a wireless connection. Communication device(s) 1410 may be configured to transmit and/or receive communication media.

Those skilled in the art will realize that storage devices used to store computer readable instructions may be distributed across a network. For example, an apparatus 1400 may communicate with a remote device 1414 via a network 1412 to store and/or retrieve computer-readable instructions to implement one or more example embodiments provided herein. For example, an apparatus 1400 may be configured to access a remote device 1414 to download a part or all of the computer-readable instructions for execution. Alternatively, an apparatus 1400 may be configured to download portions of the computer-readable instructions as needed, wherein some instructions may be executed at or by the apparatus 1400 and some other instructions may be executed at or by the remote device 1414.

In this application, including the definitions below, the term "module" or the term "controller" may be replaced with the term "circuit." The term "module" may refer to, be part of, or include processing circuitry 402 (shared, dedicated, or group) that executes code and memory hardware (shared, dedicated, or group) that stores code executed by the processing circuitry 402.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processing circuitry 402 may encompass a single microprocessor that executes some or all code from multiple modules. Group processing circuitry 402 may encompass a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The example embodiments of apparatuses and methods described herein may be partially or fully implemented by a special-purpose computer created by configuring a general-purpose computer to execute one or more particular functions embodied in computer programs. The functional blocks and flowchart elements described herein may serve as software specifications, which may be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

G. Conclusion and Use of Terms

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "component," "module," "system", "interface", and the like are generally intended to refer to a computer-related entity, either hardware, a combination of hardware and software, software, or software in execution. For example, a component may be, but is not limited to being, a process running on processing circuitry 402, processing circuitry 402, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, some example embodiments may include a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. The articles "a" and "an" as used herein and in the appended claims may generally be construed to mean "one or more" unless specified otherwise or clear from context to be directed to a singular form.

Although the disclosure has been shown and described with respect to some example embodiments, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated some example embodiments of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

H. Additional Information

Existing data archive systems typically comprise an online archive for inactive data. The data maintained in such an archive is not accessible from the application that is the source of the data. The data structure of such archives is identical to that of the source (e.g., a subsetted data model). The data stored in such systems may be periodically appended from the source. These data archive solutions offer a fast time to market and provide immediate relief to the source system in terms of performance, availability, and management.

However, such existing systems are limited in a number of ways. Notably, such systems involve replicating the source system data model for the archive, which presents a number of disadvantages once the source system becomes outdated or non-existent. Complex, normalized, and sometimes proprietary data models are understood by a select few experts, and perhaps become non-existent as source systems are eventually replaced or simply shutdown. Typically, archives that use source system schemas must evolve the archive schemas each time the source schema is changed or deal with a new version of the schema at each change.

Further, even when the system is in use, certain disadvantages may exist. For example, the source system may require source system application metadata, rules, or configurations to make sense of the data—this would not be available in the archive—the archive would consist of a random collection of unintelligible data. Archive data, using the source system data format, may encounter a proprietary format that requires vendor specific products to manage the data and a limited, perhaps proprietary set of data access methods and tools. Archiving data, in isolation, at the system level prevents centralized enterprise management and is difficult to access and secure.

As source system data identified for archive ages beyond its useful operational life, it should be archived to a separate archive platform for the remainder of its legal retention life, potentially outliving the source system itself. The long-term data archive systems and methods of the present disclosure provide a generic architecture for centralized long-term data retention.

In accordance with the present disclosure, an archive system is provided that is superior to existing archive solutions. More particularly, in one example embodiment, the present disclosure provides a generic and flexible modeling method for data archival. In connection with example embodiments of the present disclosure, any industry business model may be represented in a meta-model of generic business classes with schema-less business structures, either as a stand-alone or connected system archive. In one example embodiment, source system archive data is tagged and linked to business classes. Business data may be stored as business objects in a flexible, system-independent format.

Example embodiments of the present disclosure involve an enterprise archive system that may be comprised of disparate systems connected with enterprise master data management structures. In accordance with example embodiments of the present disclosure, an enterprise data model is not used and, instead, the data structure is object-based. The archive system is designed such that the complexity of the source system is decoupled and the data model is simplified through de-normalizing and flattening techniques. Such archive provides an effective long-term retention for inactive data that has been identified for archive. A common user interface can be used for searching and retrieving data associated with all source systems, thereby making the data available for historical customer inquiry, legal compliance and other uses such as analytics.

The long-term archive system of the present disclosure employs a class-object meta-model, an example of which is shown in FIG. 6. The model shown in FIG. 6 is example only. This example model is one that may be applicable in the health insurance industry. As will be understood by those skilled in the art, the present disclosure may be applicable to data generated by any industry; furthermore, the disclosure may use many meta-models for different aspects of its data—one for each industry. As illustrated in FIG. 6, the customer may be associated with a healthcare provider (e.g., primary physician) and an account. The customer may have made one or more healthcare insurance claims for a given provider, and data regarding the same may be processed and stored by a particular system. Similar data may be used in several of the organization's applications/systems. The data from all such applications/systems may be organized in accordance with the model.

In one example embodiment, the long-term archive meta-models, one for each industry, simplify and connect dissimilar systems at an enterprise level. A de-normalized, flattened meta-model may decouple the simple and intuitive archive structure from the complexity of source system data schemas, eliminating the need to understand the plurality of source computer system models. Source system data structures, particularly transaction systems, may have a normalized data model optimized for additions, deletions, and modifications of data. Increased separation and isolation of data (e.g., more tables, relationships) and increasing complexity may result. In one example embodiment, the archive, which is immutable, is a de-normalized data model optimized for reading data. The result may be that data is collapsed or flattened into a small number of objects—simplified and intuitive. A single meta-model enables legal and customer investigatory inquiry users to access archive data, across all systems, without requiring knowledge of each source system's unique data schema and schema evolution. By centralizing and connecting dissimilar data, the archive may become a single-copy, multi-purpose data store, supporting other use cases and opportunities of actionable insights, such as analytics.

In one example embodiment, the long-term archive employs an object-based approach to manage, store and relate dissimilar data within a centralized enterprise archive. The structure of the data object 216 is illustrated in FIG. 7. In an example embodiment, there are two classes of data objects: System Objects and Global Objects. System Objects, sourced from individual application systems, contain business data. Global Objects, sourced from enterprise master data sources, provide a key used to connect selected System Objects and provide an enterprise view, acting as the glue connecting the plurality of source computer system archives.

In one example embodiment, data objects have a consistent structure, comprising a metadata envelope and a business data payload, as shown in FIG. 8. In one example embodiment, the metadata envelope is used by the archive system to manage the data object. In one example embodiment, the envelope (metadata) is the same format for all object classes, regardless of industry. In one example embodiment, the immutable business data payload format is a schema-less, flexible format that is specific to the source system. In one example embodiment, this eliminates the complexity of schema evolution and is used for data retention and inquiry.

For example, in the healthcare industry, source systems A and B may be mapped to a "Customer" archive object class. In one example embodiment, the format (data fields) of the object envelope is the same for both source systems. However, the format (data fields) of the object payload may be different—i.e., specific to the individual source system's data attribution. By way of further example, in the healthcare industry, there is a "Claim" object class. Data for a single claim stored in many source tables is archived into a single claim object instance, in accordance with the "Claim" object class.

One possible technical advantage of the present disclosure is that structures of the source data may vary between the plurality of source systems. For example, the archive payload may be any format i.e. XML, JSON, etc. In one example embodiment, this is transparent to the user as all data is presented in a relational format through the use of views. The archive access layer abstracts the payload format from the access format by placing a relational view over the payload for SQL based access. Another important aspect may be that use of a single industry object class model with global class objects allows for a connected, cross-system enterprise archive with the flexibility of source system specific business data attribution by virtue of schema-less object payloads. Such a system enables querying and centrally managing archive data across systems. The use of master global objects—e.g., an individual who is linked to each system's customer data object—provide a connection among systems. Further, global object classes connect dissimilar archive systems providing departmental, enterprise, and other views. No enterprise archive data attribute model is required; the business data format is schema-less at the system level. The extensible and incremental object model may allow for evolution over time rather than an extensive up-front activity associated with archiving. The open and portable architecture allows for technology agnostic implementations. The flexible business data structure supports archival of structured, semi-structured and unstructured data.

Each periodic system archive, grouped into an archive package, is independent of any other for that system. Each package is a wholly self-contained archive, requiring no references to other packages or data objects in the long-term archive. An archive package provides a current point-in-time view of the source system data structure; this does not require previous archive packages to be "updated" if the source system data structure changes. As source systems data structure evolve overtime, no changes occur to the existing archive. This simplifies and ensures point-in-time historical integrity.

The components of the long-term archive, in an example embodiment, are now described, with reference to FIG. 13. A policy engine 1301 may be comprised of a computer processor. Policy engine 1301 may serve as a secure and automated means to codify a set of rules and management processes around archived data. As such, the policy engine 1301 may have rules to manage the data throughout the remainder of its life cycle. For example, retention policies may be codified in the policy engine 601 and used to determine when to eventually purge the data from the archive by interrogating an objects metadata envelope. Claims for a particular system data may be purged after 15 years while other object data may be purged on a different schedule. The policy engine 1301 may provide an automated process to manage archive data. Archive Processes 1302, examples of which are shown, may take actions on the archived data throughout its lifecycle in the long-term archive, starting with ingestion and ending with removal. Archive services 303 may provide a secure, accessible, compliant and efficient archive platform Archive services 1303 may provide a set of independent actions a user can take on the data in the archive. Ingestion may be defined as an automated load process to bring extracted source system data in the archive. Hold may be defined as an automated process to flag data and/or prevent purging. Hold may be initiated/requested by legal services in anticipation of or during litigation. Release may be defined as an automated process to un-flag data, allowing purging. Release may be initiated and/or requested by legal services after litigation. Export may be defined as an ability to extract data from the archive into a desired format. Export may occur in bulk and/or in singleton query. Purge may be defined as an automated process to remove data from the archive. Purge may occur in conjunction with the policy engine.

An example of the data extraction process is now described in more detail. Data extraction may provide a means to transform and organize the complex source data into the archive objects of the industry model. In one example embodiment, the extract design goals are to emphasize simplicity, generality, and durability (e.g., usability over time), in a format that is both human-readable and machine-readable. Separate extracts may be created for each data item of interest. For example, in the insurance context, the extracts may include policy, money, claim, and party data. In an example embodiment, the extract format is Extensible Markup Language (XML). Each XML extract has an XML Schema (e.g., XSD file) defining the structure of the extract. In one example embodiment, each extract is comprised of one or more files, if needed for size constraints. The content of the extract includes selected business data from the source system; primary and foreign key identifiers; and de-coded values from the source system.

FIG. 9 illustrates an example system for carrying out the methods of the present disclosure. A plurality of source computer systems 900a, 900b, . . . 900n may be maintained. Each of the source computer systems may store data 901a, 901b, . . . 901n. In one example embodiment, at least one of the plurality of source computer systems stores the data in a first structure and format and at least one other of the plurality of source computer systems stores the data in a second structure and format. The first structure and format may be different from the second structure and format. Data may be extracted by a computer processor 902, from the plurality of source computer systems. In one example embodiment, the extracted data is stored in an archive data storage system 903 in accordance with an industry specific model. In one example embodiment, extracted data is stored in an archive data storage system 903 in accordance with a simplified industry specific model. The industry specific model 904 (e.g., as illustrated in FIG. 6) includes at least one data object 905 (e.g., as illustrated in FIG. 7). In one example embodiment, each data object comprises metadata and a payload. In one example embodiment, the metadata is the same for each of the plurality of source computer systems and the payload is different for at least one of the plurality of source computer systems.

FIG. 10 illustrates an example system for carrying out the methods of the present disclosure. A plurality of source systems 1000a may be maintained. Each of the source systems 1000a may store data. In one example embodiment, at least one of the plurality of source computer systems stores the data in a first structure and format and at least one other of the plurality of source systems stores the data in a second structure and format. The first structure and format may be different from the second structure and format. Data may be mapped by a computer processor from the plurality of source systems 1000*a* to meta-model 1000*b*. In one example embodiment, the mapped data is stored in an archive repository, 1000*c*, in accordance with an industry specific model.

The present disclosure may reflect an improvement to computer systems and technology. The present disclosure may result in improvements in data storage associated with a long-term data archive system, achieving a number of benefits as described more fully herein. De-normalized, flattened archive industry object class models may be simple and intuitive. Industry object class models may decouple the archive from the complexity of unique source system schemas. Global object classes may connect dissimilar archive systems providing departmental, enterprise and other views. Business data formats may be schema-less at the system level. Separate archive object models may remove the need to deal with the evolution of source system schemas. Extensible and incremental object models may allow for an evolution over time rather than an extensive up-front activity. Multi-purpose archives may support other use cases and/or opportunities of actionable insights. Open and portable architecture may allow for technology agnostic implementations. Flexible business data structures may support structured, semi-structured and unstructured data.

The invention claimed is:

1. An apparatus comprising:
a non-transitory computer-readable medium storing instructions; and
processing circuitry configured by the instructions to archive a data set provided by a set of data sources stored in a plurality of locations by:
determining an industry object model for the data set, and
generating an archive package for an archive time point by:
generating a set of global objects such that each global object of the set of global objects is represented in the data set, and
for a respective data source of the set of data sources:
generating a set of data source objects based on the industry object model by:
determining archival data of the respective data source to be archived, and
transforming the archival data of the respective data source into a set of data source objects based on the industry object model;
associating the set of data source objects with the set of global objects, and
storing, in the archive package, the set of data source objects and the set of global objects for the respective data source.

2. The apparatus of claim 1 wherein the industry object model is determined based on an industry of the data set.

3. The apparatus of claim 1 wherein the processing circuitry is configured to:
receive a request to access the archive package based on an access criterion; and
provide access to the archive package according to the access criterion.

4. The apparatus of claim 1 wherein:
the industry object model includes a set of industry objects representing entities or units of data within an industry of the data set,
the processing circuitry is configured to transform the archival data of the respective data source into the set of data source objects by:
receiving a transform provided by the respective data source; and
invoking the transform to generate at least one data source object of the set of data source objects as a record including a set of metadata fields and a business data block, and
the record corresponds to at least one of the set of industry objects.

5. The apparatus of claim 1 wherein the processing circuitry is configured to identify a subset of the set of data source objects to be purged based on a purge time point and a policy engine.

6. The apparatus of claim 5 wherein the processing circuitry is configured to identify the subset of the set of data source objects to be purged, by:
evaluating the set of data source objects to identify the subset of the set of data source objects to be purged based on a set of purge rules of the policy engine.

7. The apparatus of claim 6 wherein the set of purge rules of the policy engine include at least one of:
a hold rule to place a hold on a data source object,
a hold release rule to release a hold on a data source object, and
a purge rule to purge data source objects on which a hold has not been placed.

8. The apparatus of claim 1 wherein the processing circuitry is configured to:
store an audit trail of events involving the archive package; and
responsive to detecting an event involving the archive package, log the event in the audit trail.

9. The apparatus of claim 8 wherein the processing circuitry is configured to:
receive a selection of a subset of events to be logged in the audit trail; and
refrain from logging the event based on determining that the event is not within the subset of events to be logged in the audit trail.

10. A non-transitory, computer-readable medium comprising instructions that include:
determining an industry object model for a data set provided by a set of data sources stored in a plurality of locations; and
generating an archive package for an archive time point by:
generating a set of global objects such that each global objects of the set of global objects is represented in the data set, and
for a respective data source of the set of data sources:
generating a set of data source objects based on the industry object model by:
determining archival data of the respective data source to be archived, and
transforming the archival data of the respective data source into the set of data source objects according to the industry object model,
associating the set of data source objects with the set of global objects; and storing, in the archive package, the set of data source objects and the set of global objects for the respective data source.

11. The non-transitory, computer-readable medium of claim 10 wherein:
  transforming the archival data includes:
    receiving a transform provided by the respective data source, and
    invoking the transform to generate at least one of the set of data source objects as a record comprising a set of metadata fields and a business data block;
  the industry object model includes a set of industry objects representing entities or units of data within an industry of the data set; and
  the record corresponds to at least one of the set of industry objects.

12. A method of archiving a data set provided by a set of data sources stored in a plurality of locations, the method comprising:
  determining an industry object model for the data set; and
  generating an archive package for an archive time point by:
    generating a set of global objects such that each global objects of the set of global objects is represented in the data set, and
    for a respective data source of the set of data sources:
      generating a set of data source objects based on the industry object model by:
        determining archival data of the respective data source to be archived, and
        transforming the archival data of the respective data source into the set of data source objects according to the industry object model;
      associating the set of data source objects with the set of global objects, and
      storing, in the archive package, the set of data source objects and the set of global objects for the respective data source.

13. The method of claim 12 wherein the industry object model is determined based on an industry of the data set.

14. The method of claim 12 wherein transforming the archival data of the respective data source into the set of data source objects includes:
  receiving a transform provided by the respective data source; and
  invoking the transform to generate at least one data source of the set of data source objects as a record including a set of metadata fields and a business data block, wherein:
    the industry object model includes a set of industry objects representing entities or units of data within an industry of the data set, and
    the record corresponds to at least one of the set of industry objects.

15. The method of claim 12 further comprising:
  identifying a subset of the set of data source objects to be purged based on a purge time point and a policy engine, and
  after generating the archive package, removing data for each entity that is archived in the archive package from the data set.

16. The method of claim 12 further comprising:
  for each respective data source, creating in the archive package a system data source object that represents the respective data source,
  wherein storing the set of data source objects for each respective data source includes associating each data source object with the system data source object for the respective data source.

17. The method of claim 12 further comprising:
  receiving a request to access the archive package based on an access criterion; and
  providing access to the archive package according to the access criterion.

18. The method of claim 12 further comprising:
  receiving a request to export the archive package, the request indicating an export format; and
  exporting the archive package according to the export format.

\* \* \* \* \*